US008876811B2

(12) United States Patent
Lewinsky et al.

(10) Patent No.: US 8,876,811 B2
(45) Date of Patent: Nov. 4, 2014

(54) TISSUE TREATMENT APPARATUS AND METHODS

(75) Inventors: Reuven M. Lewinsky, Alonel Aba (IL); Roee Khen, Haifa (IL)

(73) Assignee: Lumenis Ltd. (IL)

( * ) Notice: Subject to any disclaimer, the term of this patent is extended or adjusted under 35 U.S.C. 154(b) by 0 days.

(21) Appl. No.: 13/588,275

(22) Filed: Aug. 17, 2012

(65) Prior Publication Data

US 2012/0316549 A1 Dec. 13, 2012

Related U.S. Application Data

(63) Continuation of application No. 12/755,142, filed on Apr. 6, 2010, now abandoned.

(60) Provisional application No. 61/182,649, filed on May 29, 2009, provisional application No. 61/167,452, filed on Apr. 7, 2009.

(51) Int. Cl.
*A61B 18/22* (2006.01)

(52) U.S. Cl.
CPC ......... *A61B 18/22* (2013.01); *A61B 2018/2272* (2013.01)
USPC .......................................................... 606/16

(58) Field of Classification Search
CPC .................. A61B 18/20; A61B 18/22; A61B 2018/2272; E06B 3/2675
See application file for complete search history.

(56) References Cited

U.S. PATENT DOCUMENTS

| | | | |
|---|---|---|---|
| 3,982,541 A | 9/1976 | L'Esperance | |
| 4,240,431 A * | 12/1980 | Komiya | 606/15 |
| 5,090,908 A * | 2/1992 | Teumim-Stone | 433/215 |
| 5,196,004 A | 3/1993 | Sinofsky | |
| 5,300,087 A | 4/1994 | Knoepfler | |
| 5,562,657 A | 10/1996 | Griffin | |
| 5,906,625 A * | 5/1999 | Bito et al. | 606/142 |
| 6,454,762 B1 | 9/2002 | Rosler et al. | |
| 6,530,921 B1 * | 3/2003 | Maki | 606/15 |
| 6,599,287 B2 * | 7/2003 | Iwahashi et al. | 606/14 |
| 6,673,065 B1 | 1/2004 | Veligdan | |
| 6,743,221 B1 * | 6/2004 | Hobart et al. | 606/4 |
| 7,238,180 B2 | 7/2007 | Mester et al. | |
| 2005/0021078 A1 | 1/2005 | Vleugels et al. | |
| 2005/0283144 A1 * | 12/2005 | Shiono et al. | 606/18 |
| 2008/0064982 A1 | 3/2008 | Nowlen et al. | |
| 2008/0319442 A1 * | 12/2008 | Unger et al. | 606/48 |

FOREIGN PATENT DOCUMENTS

| | | |
|---|---|---|
| DE | 4434938 C1 | 2/1996 |
| EP | 0610991 A2 | 8/1994 |

\* cited by examiner

*Primary Examiner* — William Thomson
*Assistant Examiner* — Scott T. Luan
(74) *Attorney, Agent, or Firm* — Isus Intellectual Property PLLC

(57) ABSTRACT

Disclosed are apparatus, method, devices and instruments, including an apparatus that includes a flexible waveguide coupled to a supporting structure, and further coupled to a treatment tip. The apparatus also includes a beam controller to control application of a radiation beam emitted from the flexible waveguide to distribute the beam over an area different than an area covered by direct application of the beam to a single location on a target tissue. Further disclosed is an apparatus that includes a waveguide, coupleable to a laser source, and a thermal protection instrument. The thermal protection instrument includes a tissue contacting member to contact a part of an area of a tissue irradiated by laser radiation, and a beam blocking element to absorb at least some of radiation not absorbed by the area of the tissue, the beam blocking element being thermally isolated from the area of the tissue.

10 Claims, 16 Drawing Sheets

TISSUE TREATMENT APPARATUS AND METHODS

CROSS-REFERENCE TO RELATED APPLICATIONS

This application claims priority to provisional U.S. application Ser. No. 61/167,452, entitled "Tissue Treatment Devices and Methods," filed Apr. 7, 2009, and provisional U.S. application Ser. No. 61/182,649, entitled "Apparatus and Method for Treating Tissue," filed May 29, 2009, the contents of all of which are hereby incorporated by reference in their entireties.

BACKGROUND

Many operations inside the abdominal cavity are currently performed by laparoscopy, a minimally invasive procedure associated with decreased risk, shorter recovery time and improved aesthetics (fewer scars, etc.). In performing a laparoscopy procedure, a rigid viewing apparatus (laparoscope) is inserted via a small incision adjacent to the umbilicus, and one or more accessory punctures are used to introduce various treatment tools for grasping, cutting, suturing and achieving hemostatic control. Safe and effective laparoscopic surgery requires having a clear view of the area and target to be treated, and the availability of a variety of tools (some of which may be energized) to perform the surgical procedure. The laparoscope and the treatment devices are generally introduced into the abdominal cavity via trocars which provide a port of entry.

Recently, the trend towards minimally invasive surgery (MIS) has taken further steps to further minimize the extent of abdominal wall scarring while maintaining a high level of efficacy and user control. Procedures which are part of this approach include single port or single trocar laparoscopy, natural orifice translumenal endoscopic surgery (NOTES) and robotic surgery. These procedures require new tools with added maneuverability, especially to facilitate the ability to rotate the treatment tip and add spatial degrees of freedom to the tool's tip. This added flexibility enables performing surgical procedures (in the abdomen and other areas of the body) using a single trocar through which several surgical devices/instruments, including a laparoscope or an endoscope, are passed into the abdominal cavity.

One of the advantages of using laser waveguides is their flexibility. Specifically, laser waveguides can be deflected to a radius of several centimeters, depending on the waveguide diameter, materials the waveguide are made from and other structural characteristics. While hollow waveguides are less flexible than solid fibers, the advantage of hollow wave guides is their capability to deliver long wavelengths in the IR range, for example, $CO_2$ and Er:YAG wavelengths radiation with high power. Because $CO_2$ lasers are considered to be the ideal laser scalpel, the ability to use waveguides to deliver $CO_2$ radiation is important for laparoscopic and other surgical procedures.

Laser surgery uses a high energy laser radiation beam which can, for example, cut, ablate and/or coagulate the tissue. The efficiency, precision and resultant minimal collateral damage characterizing laser devices make them suitable for use in laparoscopic procedures, as well as other types of procedures, in a manner similar to the way laser-based devices have become widespread in performing various surgical procedures in a variety of medical specialties. For example, laser assisted laparoscopic surgery has been performed by transmitting laser radiation, e.g., generated by $CO_2$ lasers, via a straight rigid laparoscope. However, use of such a laparoscope to enable laser-based operations puts limitations on the procedure.

A challenge associated with the use of laser energy to perform procedures is the risk of damage that may be caused to surrounding non-targeted tissue. For example, a $CO_2$ laser beam exiting a hollow waveguide can be of high energy and be minimally dispersing with distance (and therefore may have an advantage over traditional RF or ultrasound based instruments), but, however, carries a risk when the laser beam unintentionally hits a non targeted tissue. To overcome this risk, a backstop protector is sometimes used where the treated tissue is placed between the laser waveguide tip and the backstop. However, as the tissue is being cut, stray laser radiation may hit the backstop and a gradual effect of heating is induced. In turn, heat conduction processes may cause heat to be delivered from the backstop to the tissue and may thus cause collateral damage to the tissue, as well as cause the tissue to stick to the backstop.

It is to be noted that unlike RF or ultrasound based instruments, where the direct heat transfer from the heated part of the tool to the tissue is the mechanism which causes the treatment effect (e.g., either cutting or coagulating), the laser energy does not require such conduction, and in fact the tissue is "floating" and can be cut from a distance.

A further challenge involved with using laser energy in procedures (e.g., surgical procedures) is the delivery of laser energy in conjunction with the use of other tools (e.g., graspers) to manipulate the tissue. For example, in treating tissue, grasping instruments (or graspers) may sometimes be used. Implementations of grasping laparoscopic instruments include instruments that have a hollow shaft with a typical outer diameter of 5 mm which has a controlling handle at its proximal side and a treating tip coupled to the shaft's distal end. The treatment tip generally has one or two moveable jaws which may be closed against each other using the controls at the handle. In more advanced instruments, an additional hinge may be placed at some distance from the tip which enables bending the tip with respect to the instrument's shaft at angles of up to about 90°. Such a structure requires passing a laser waveguide inside the instrument's main shaft, and allowing it to be bent at the flexible hinge proximal to the instrument's tip. The limited bending angle of the waveguide and the limited space available at the treatment tip to deflect the beam make it difficult to implement scanning movement of radiation, either linear or radial (rotational), of the beam over the target tissue.

SUMMARY

The present disclosure is directed to apparatus, systems, devices and methods to perform procedures, e.g., laparoscopic procedures, to deliver laser energy to a target tissue by using waveguides and beam controllers. In some embodiments, the disclosed treatment apparatus/devices are separate from viewing devices (laparoscope or endoscope).

In some implementations of the present disclosure, controlled delivery of radiation (laser) energy may be performed in one of several ways:

1) A waveguide follows a curved channel such that the beam emitted from its tip hits the tissue in an essentially perpendicular direction (relative to the tissue) and can scan the target tissue by a back and forth linear motion.

2) A waveguide tip is received in a separate curved beam-conducting-element, e.g., an element constructed from silver or some other material, and the curved element can then scan the target tissue by, for example, back and forth linear motion.

3) An energy beam exiting a waveguide hits a fixed reflective surface which can be flat or curved. When curved in a specific way, the surface's curved nature causes the spot to be converted into a long and thin ellipse thus creating a sharp scalpel like cut in the tissue.

4) An energy beam exiting a waveguide hits a flat (optionally concave) mirror which diverts it towards the tissue. By controllably moving the mirror back and forth, the beam scans the tissue (in some embodiments, the scanning is substantially perpendicular to the surface of tissue). The mirror is thus configured as a scanning apparatus which moves back and forth to create a line.

The present disclosure is also directed to avoiding causing tissue to stick to or thermally damaged by a heated backstop or a heated opposite jaw of a grasper. In some embodiments, the disclosed apparatus/devices are implemented based on a "no-touch" or "floating tissue" principle. Specifically, in some embodiments, the backstop, or opposite jaw of a grasping instrument, may have a double or triple layer configuration. The energy beam crossing the tissue passes through a slit in a heat insulating layer and hits, for example, a metal part of the backstop or jaw of the grasping device. Even in circumstances where the jaw heats to very high temperatures, the heat does not reach the tissue because it floats on the heat insulating layer, thus preventing tissue from being "baked" on the heated metal part and sticking to it. This results in a clean, precise cut with minimal collateral thermal damage.

The apparatus, devices and methods described herein may be used to perform procedures such as, but not limited, to laparoscopy, laryngology, Ear-Nose-Throat procedures, thoracoscopy, orthopedics or other application in open and endoscopic surgery. The apparatus, devices and methods described herein may also be used in other applications (e.g., industrial applications).

In one aspect, an apparatus is disclosed. The apparatus includes a flexible waveguide coupled to a supporting structure, and further coupled to a treatment tip, the flexible waveguide being coupleable to a laser source generating laser radiation and configured to deliver the laser radiation and to emit a beam of the generated laser radiation from a distal end of the flexible waveguide to irradiate a target tissue of a patient. The apparatus also includes a beam controller to control application of the radiation beam emitted from the flexible waveguide to distribute the beam over an area different than an area covered by direct application of the beam to a single location on the target tissue.

Embodiments of the apparatus may include any of the following features.

The beam controller configured to control application of the radiation beam may be configured to cause spatial movement of the distal end of the waveguide.

The waveguide may be integrated into the treatment tip.

The flexible waveguide may include a flexible waveguide configured to direct laser radiation generated by a CO2 laser system.

The treatment tip may include one or more grasping jaws to grasp at least part of the tissue of the patient. The one or more grasping jaws may include a fixed grasping jaw, and a moving grasping jaw configured to controllably move relative to the fixed grasping jaw.

The radiation emitted from the distal end of the flexible waveguide may be passed through a dedicated opening defined in the treatment tip before the radiation is applied to the target tissue.

The beam controller may include a reflector to direct the radiation, emitted from the distal end of the flexible waveguide, to the target tissue.

The apparatus may further include a housing containing the reflector, with the flexible waveguide being fixedly secured to the housing such that the distal end of the flexible waveguide is maintained in a fixed position relative to the housing.

The reflector may define a substantially concave surface in one direction and may further define a convex surface in another direction, the surfaces of the reflector causing the radiation to be reflected from the surfaces to be distributed substantially uniformly to form a shape of a line on the cut tissue.

The reflector may include a scanning reflector configured to spatially move to direct the radiation emitted from the distal end of the flexible waveguide to different locations on the target tissue. The scanning reflector may be configured to converge the reflected beam to a shape of a small spot.

The beam controller may include a curved spatial reflector having pre-determined geometry and configured to direct the radiation emitted from the distal end of the flexible waveguide so that the directed radiation is substantially distributed over a section in the target tissue according to a pre-determined cutting geometry resulting from the pre-determined geometry of the curved spatial reflector. The resulting shape may be similar to one of an ellipse and/or a rectangle, with one axis of the one of the ellipse and the rectangle having narrow dimensions such that a resulting cut in the tissue is substantially a thin line.

The beam controller may include an actuator to actuate at least the distal end of the flexible waveguide to cause the distal end of the flexible waveguide to spatially move.

The actuator configured to actuate the at least the distal end of the flexible waveguide may be configured to actuate the at least distal end of the flexible waveguide to cause the radiation emitted from the distal end of the flexible waveguide to be applied to different locations of the target tissue in a scanning pattern.

The beam controller may be further configured to control the power density of the laser radiation by varying the distance between the distal end of the flexible waveguide and the target tissue.

The beam controller may include a controllably displaceable scanning tip coupled to the waveguide, and an actuator to actuate the scanning tip, the actuation of the scanning tip causing the scanning tip to be controllably displaced to apply the radiation energy delivered via the waveguide to different locations of the target tissue in a scanning pattern. The waveguide further may include the scanning tip.

The actuation of the scanning tip causing the tip to be controllably displaced may cause one or more of, for example, controllable linear displacement and/or controllable radial displacement of the scanning tip over an angular range.

The scanning tip coupled to the waveguide may be secured to the treatment tip.

The treatment tip may include an inner channel extending to an opening defined on an external surface of the treatment tip, the inner channel structured to receive at least a portion of the waveguide.

The apparatus may further include a moveable radiation protector to, when actuated to a blocking position, prevent radiation emitted from the distal end of the flexible waveguide from propagating beyond the target tissue of the patient.

The supporting structure may include one or more of, for example, a hollow tube, a shaft, and/or a scope-based device.

The treatment tip may pivotably coupled to the supporting structure at a hinged location.

In another aspect, a method is disclosed. The method includes coupling a flexible waveguide configured to deliver laser radiation to a treatment tip coupled to a supporting structure, coupling the laser radiation generated by a laser source to the flexible waveguide, and controlling application of a radiation energy beam emitted from a distal end of the flexible waveguide to distribute the beam over an area different than an area covered by direct application of the beam to a single location on a target tissue of a patient.

Embodiments of the method may include one or more of the above-described features of the apparatus.

In a further aspect, an apparatus is disclosed. The apparatus includes a waveguide coupleable to a laser source generating laser radiation and a thermal protection instrument. The thermal protection instrument includes a tissue contacting member to contact a part of an area of a tissue irradiated by laser radiation emitted from an emitting end of the waveguide, and a beam blocking element to absorb at least some of radiation not absorbed by the area of the tissue, the beam blocking element being thermally isolated from the area of the tissue.

Embodiments of the apparatus may include one or more of the above-described features of the first apparatus and/or the method, as well as any of the following features.

The tissue contacting member may include an opening to enable the at least some of the radiation not absorbed by the area of the tissue to reach the beam blocking element.

The thermal protection instrument may further include a thermal insulation layer positioned between the tissue contacting member and the beam blocking element. The tissue contacting member and the thermal insulation layer may include at least partly overlapping respective openings to enable the at least some of the radiation not absorbed by the area of the tissue to reach the beam blocking element.

The tissue contacting member may be a thermally insulation layer.

The thermal protection instrument may be a backstop coupleable to a supporting structure.

The thermal protection instrument may further include an external thermal insulation layer coupled to an external-facing surface of the beam blocking element, the external thermal insulation layer configured to prevent thermal damage to neighboring tissue areas.

The apparatus may further include a grasping device including an energy emitting member coupled to the emitting end of the waveguide, the energy emitting member configured to grasp another part of the area of the tissue being treated, and the thermal protection instrument, with the tissue contacting member of the thermal protection instrument being positioned opposite the energy emitting member.

The radiation emitted from the emitting end of the waveguide may be passed through an opening defined in the energy emitting member before the radiation is applied to the area of the tissue being irradiated, and the at least some of the radiation not absorbed by the area of the tissue is passed through another opening defined in the tissue contacting member such that the at least some of the radiation not absorbed by the area of the tissue is received by the beam blocking element.

The apparatus may further include a beam controller to control direction of the radiation emitted by the waveguide to apply the radiation to different locations of the area of the tissue. The beam controller may include one or more of, for example, a reflector to direct the radiation emitted from the emitting end of the waveguide to the area of the tissue, an actuator to actuate at least the emitting end of the waveguide to cause the emitting end of the waveguide to spatially move, and/or a controllably displaceable scanning tip coupled to the waveguide and an actuator to actuate the scanning tip, with the actuation of the scanning tip causing the scanning tip to be controllably displaced to apply the radiation energy delivered via the waveguide to different locations of the area of the tissue in a scanning pattern.

The apparatus may further include a heat removal mechanism to remove heat resulting from at least some of the absorbed radiation from the beam blocking element.

The apparatus may further include a thermal sensor to measure the temperature of the beam blocking element.

The apparatus may further include a controller to control the radiation emitted from the emitting end of the waveguide based on the measured temperature of the beam blocking element.

In yet another aspect, a method is disclosed. The method includes contacting a part of an area of a tissue with a tissue contacting member coupled to a beam blocking element, the beam blocking element being thermally isolated from the area of the tissue. The method also includes applying laser radiation to the area of the tissue, wherein at least some of the radiation not absorbed by the area of the tissue is absorbed by the beam blocking element, the thermal isolation of the beam blocking element from the area of the tissue substantially preventing heat resulting from the at least some of the radiation absorbed by the beam blocking element from being directed to any part of the area of the tissue.

Embodiments of the method may include one or more of the above-described features of the first and second apparatus and first method, as well as any of the following features.

Contacting part of the area of the tissue with the tissue contacting member may include contacting part of the area of the tissue with the tissue contacting member coupled to a thermal insulation layer positioned between the tissue contacting member and the beam blocking element.

Applying laser radiation may include applying the radiation based on temperature measured at the beam blocking element.

In another aspect, a thermal protection instrument is disclosed. The thermal protection instrument includes a tissue contacting member to contact a part of an area of a tissue irradiated by laser radiation emitted from an emitting end of a waveguide, the waveguide being coupleable to a laser source to generate the laser radiation. The thermal protection instrument further includes a beam blocking element to absorb at least some of radiation not absorbed by the area of the tissue, the beam blocking element being thermally isolated from the area of the tissue.

Embodiments of the thermal protection instrument may include one or more of the above-described features of the first and second apparatus and the first and second methods.

Details of one or more implementations are set forth in the accompanying drawings and in the description below. Further features, aspects, and advantages will become apparent from the description, the drawings, and the claims.

DETAILED DESCRIPTION

Figure 1:
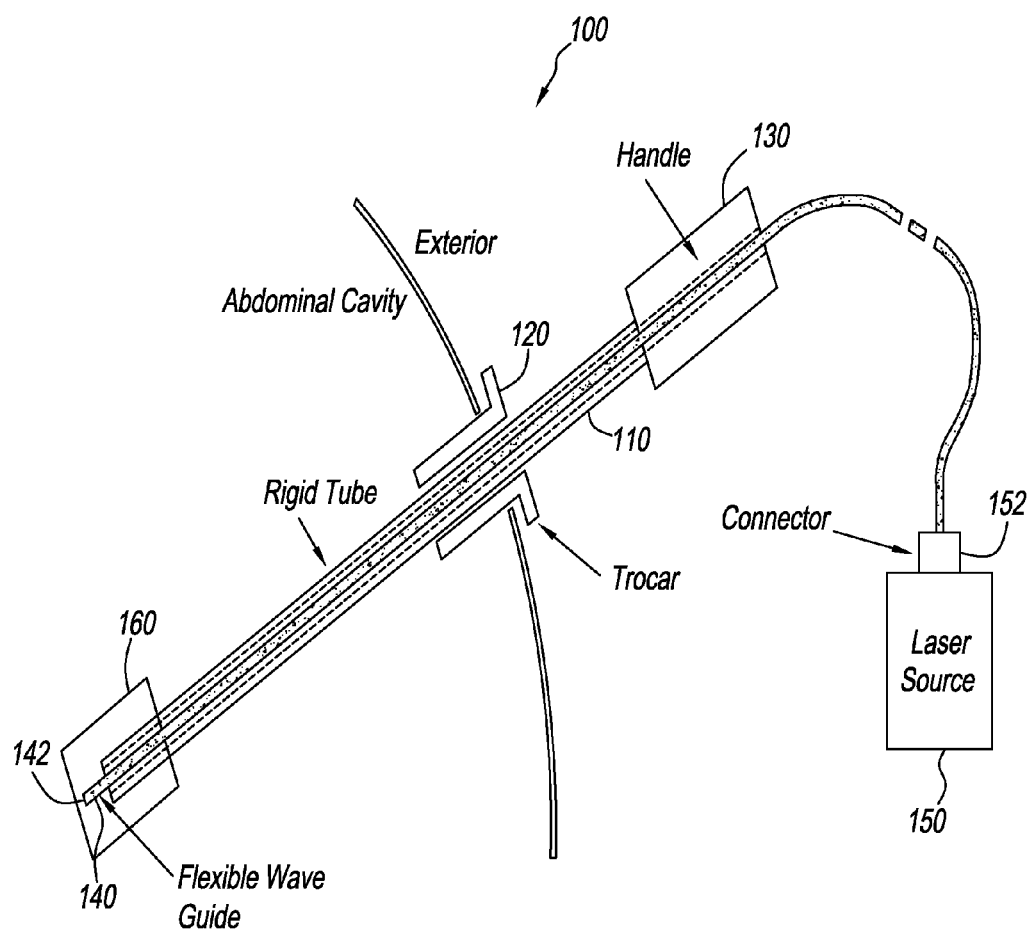
FIG. 1 is a schematic diagram of a laser assisted apparatus for laparoscopic surgery.

Described herein are apparatus, devices and methods, including an apparatus that includes a flexible waveguide coupled to a supporting structure. The flexible waveguide is coupleable to a laser source generating laser radiation, and is configured to deliver the laser radiation and to emit a beam of the generated laser radiation from a distal end of the flexible waveguide to irradiate a target tissue of a patient. The apparatus may also include a treatment tip (e.g., a grasper or some other instrument) coupled to the waveguide (in some embodiments, the waveguide is integrated into the treatment tip). The apparatus further includes a beam controller to control the application of the radiation beam emitted from the flexible waveguide to distribute the beam over an area different than an area covered by direct application of the beam to a single location on the target tissue (i.e., if the beam were applied without using the beam controller). In some embodiments, the supporting structure may be a shaft or a tubular device such as, for example, a tube, or a scope-based device (e.g., a scope-based device configured to perform laparoscopic surgery). In some embodiments, the flexible waveguide may be configured to direct laser radiation generated by a CO2 laser system. In some implementations, the beam controller may include one or more of, for example: i) a reflector to direct the radiation emitted from the distal end of the flexible waveguide to the target tissue, ii) a curved spatial reflector having a pre-determined geometry, iii) an actuator to actuate at least the distal end of the flexible waveguide to cause the distal end of the flexible waveguide to spatially move (in such implementations, the apparatus may or may not include a treatment tip), iv) a controllably displaceable distal tip (also referred to as scanning tip) coupled to the waveguide and actuated by an actuator such that the actuation of the scanning tip causes the tip to be controllably displaced to apply the radiation energy delivered via the waveguide to different locations of a target tissue (e.g., in a scanning pattern).

Also described herein are apparatus, devices and methods, including an apparatus that includes a waveguide coupleable to a laser source generating laser radiation, and a thermal protection instrument. The thermal protection instrument includes a tissue contacting member to contact a part of an area of a tissue irradiated by laser radiation emitted from an emitting end of the waveguide, and a beam blocking element to absorb at least some of radiation not absorbed by the area of the tissue. The beam blocking element is thermally isolated from the area of the tissue. In some embodiments, the apparatus may include a grasping device in which the tissue contacting member of the thermal protection instrument serves as one of the grasping members of the device, e.g., the member opposite another grasping member that is coupled to the waveguide near the emitting end of the waveguide. In some embodiments, the thermal protection instrument may include an insulation layer, positioned between the tissue contacting member and the, optionally metallic, beam blocking element that may be used to prevent heat from the beam blocking element to be conducted to the tissue.

Tissue Treatment Apparatus with Flexible Waveguides

A laparoscopic surgery apparatus generally includes a device with a shaft having a typical length of about 30-40 cm. coupled to the shaft is a treatment tip configured to perform one or more types of tissue manipulation operations such as grasping, cutting, dissection, hemostasis, etc. In some implementations, energy delivery systems/mechanisms are included with these apparatus. In some embodiments, such energy delivery systems cause part of the tip to be heated, to thus enable some desired effect to be performed on the target tissue.

A proximal part of the apparatus for laparoscopic surgery (or other types of procedures) may include a set of handles and other activators to control, for example, the spatial position and/or movement of the tip and/or energy delivery controls of the device (e.g., an ON and OFF to cause energy delivery activation).

In some embodiments, a basic apparatus for laparoscopic surgery may include a shaft passing through a trocar, a handle and an operating tip having a cutting device. This can be viewed as a scalpel connected to a shaft with a handle. Additionally, some laparoscopic surgery apparatus also include features (e.g., added tools) to enable the implementation of some type of relative movement between (typically) two parts at the tip. Such movements enable, for example, tissue grasping, dissecting, tearing, etc. In such embodiments, the tip can be rotated with respect to the apparatus' longitudinal axis.

As noted, in some embodiments, apparatus may be connected to energy delivery mechanisms and sources to, for example, enable blood vessels coagulation functionality. Typical energy sources used with conventional laparoscopic surgery devices include RF energy (mono polar or bipolar), ultrasound energy sources (as used, for example, in the Harmonic Scalpel manufactured by Ethicon Endosurgery), etc. Such energy sources may be used, for example, to heat up some element in the device's tip which in turn causes cutting of tissue and/or blood vessels coagulation to be performed by having the tip directly touch the treated tissue to thus transmit heat to it.

Referring to FIG. 1, a schematic diagram of a laser assisted apparatus 100 is shown. The apparatus 100 includes a supporting structure 110, such as a shaft, a tubular device, etc., that can be passed through a trocar 120. The apparatus also includes a flexible waveguide 140, coupled to the supporting structure 110, which directs laser energy produced by a laser source 150 onto tissue. Suitable waveguides include, for example, hollow silica waveguides with internal coatings and external protective layers.

In some implementations, the supporting structure may be a shaft, a tube, a duodenoscope, bronchoscope, urethroscope, etc., to which the waveguide is coupled. For example, where a tubular device is used (tube or scope-based device), the waveguide 140 may be passed through an inner channel of the tubular device. In some embodiments, another tubular device (e.g., a baby-scope) may be passed through the inner channel of the first tubular device, with the waveguide then passing through the other tubular device. In some implementations, the supporting structure 110 may be a shaft to which the waveguide may be secured (e.g., to the external surface(s) of the shaft).

The laser source 150 may include a CO2 laser system having a typical wavelength of approximately 10.6 µm, an isotopic $^{13}CO_2$ laser with a typical wavelength of 11.2 µm, etc., that is coupled to one end of the flexible waveguide 140. The radiation from the radiation source may be coupled to the waveguide using, for example, a connector 152 (e.g., a CO2 laser connector). Suitable laser connectors to connect the laser generating device to the waveguide may include, for example, laser SMA connectors, laser S-T connectors, etc. Other coupling arrangements (e.g., based on arrangements of optical elements) may also be used. The radiation coupled to the waveguide 140 is transmitted through the waveguide and emitted from a distal end 142 of the waveguide onto a target tissue. In some embodiments, the radiation source 150 to generate the radiation may include, for example, an Er:YAG laser system (that typically operates to generate radiation having a wavelength of approximately 2.94 µm), a Ho:YAG laser system typically operating to generate a wavelength having a wavelength of approximately 2.1 µm and/or Nd:YAG laser system emitting radiation having a wavelength of approximately 1.06 µm. Other suitable laser devices may include, in some embodiments, at least one laser diode (which may be arranged in a diode array). The at least one laser diode may include a quantum-well laser based on Antimonide (Sb) compounds such as, for example, In(Al)GaAsSb-based compounds, GaSb-based compounds, etc. In some embodiments, the first radiation source may include a specially doped fiber laser such as, for example, erbium-doped fluorozirconate and Thulium fiber laser. Other types of radiation sources may also be used.

In some embodiments, the waveguide (or other energy conduits) described herein may be used to simultaneously transmit radiation at different wavelengths. For example, in some implementations, waveguides can pass two (or more) wavelengths, e.g. 10.6 or 11.2 µm from a CO2 laser system and 2.9 µm from an Er:YAG laser. In a hollow waveguide, for example, it is possible to use the hollow part of a waveguide to transmit radiation generated by a CO2 laser system, and use the silica solid part of the hollow waveguide to transmit radiation having another wavelength, e.g. 635 or 532 nm for red or green respectively aiming beam or some treatment wavelength e.g. Nd:YAG at 1.06 µm or Ho:YAG at 2.1 µm.

The type and/or configuration of the flexible waveguide 140 to deliver the radiation generated by the radiation source 150 may be based, at least in part, on the particular radiation source used. For example, in circumstances in which the radiation source is a CO2 laser system, the waveguide 140 may be a hollow waveguide adapted to direct radiation generated by a CO2 laser device. Such a hollow waveguide may include a silica tube whose internal surface is coated with, for example, silver or other types of metals or waveguides made of polymeric layers. In some embodiments, the structure of a CO2 waveguide, such as the waveguide 140, may include several layers. In such implementations, the center of the waveguides may include the hollow part, defined by the surrounding layers, through which air or other gases may flow and inside which the radiation passes. Surrounding the hollow part is typically a thin film of Silver Iodine followed by another thin layer of silver metal. These layers may be surrounded by a silica layer with a typical wall thickness of several hundreds of microns, and the entire layered arrangement may be surrounded by a polymeric protective layer (sometime referred to as a buffer, clad or coating.)

In some embodiments, for example in implementations in which laser diode and/or laser systems to generate shorter wavelengths than those generated with a CO2 laser device, the flexible waveguide may include one or more optical fibers adapted to transmit radiation (e.g., optical radiation) having such wavelengths of, for example, 1-10 µm. Suitable waveguides to transmit optical radiation having such wavelength includes, for example, glass, silica glass, crystalline fibers, Sapphire fibers, Germanate glass fibers, a combination of Germanate glass fibers with Sapphire tip, hollow core fibers and/or any other suitable waveguides or radiation conduits to deliver laser energy.

The apparatus 100 also includes a beam controller 160 (also referred to as a beam diverting mechanism) to control the position of the radiation emitted by the flexible waveguide to distribute the beam over an area different than that covered by direct application of a beam on a surface (i.e., the resulting area if the beam were applied without use of the beam controller). For example, the area covered using the beam controller could be of a different size than the area that otherwise would have been covered, it may be in a different location, it may cover multiple locations, etc. The beam controller 160 is represented schematically as a box in FIG. 1, with more particular implementations for the beam controller described in relation to, for example, FIGS. 3-10. For example, in some implementations, the beam controller 160 may include actuation mechanisms to cause the distal end of the waveguide 110 to be displaced (linearly and/or pivotably) to direct the radiation beam at various locations of the target tissue. In some embodiments, such movement could be based on a pre-determined scanning pattern that can be achieved through, for example, automated actuation of the distal end of the waveguide (e.g., by using a processor-based computing device configured to perform operations responsive to execution of computer instructions). Additionally and/or alternatively, in some embodiments, the beam controller 160 may also control, at least partly, spatial movement of the supporting structure 110 to cause the radiation beam to be directed to different locations of the target tissue in a controlled manner.

As further shown in FIG. 1, a handle 130 to enable an operator (e.g., surgeon) to hold and control the apparatus is attached to a proximal end of the shaft. In some embodiments, the apparatus also includes a treatment tip to interact with the target tissue to be treated, e.g., manipulate the tissue to grasp it, pinch it, etc. The handle 130 may enable control of the device's various functionalities, including such functionalities as controlling the movement and orientation of the device, e.g., controlling the beam controller 160 (e.g., by controlling movement of the waveguide 140) to thus control the direction at which the radiation beam is directed (in some embodiments, the beam controller 160 may be implemented as part of the structure of the handle 130). In some embodiments, the handle 130 may comprise several individual user-controllable elements such as, for example, levers, buttons, knobs, and other types of user controllable elements. Such user-controllable elements may be arranged on the apparatus 100, for example, on the handle 130. In response to user manipulation of any one of the user controllable elements, the actuation mechanisms controlled via the one or more user-controllable elements are actuated, thus causing an associated movement or manipulation of the supporting structure 110, the waveguide 140, the treatment tip (if one is used), and any other element of the apparatus 100. Another user-controllable interfacing element could be an ON-OFF button which controls delivery of laser radiation via the waveguide 140 at the operator's discretion. Another control button can alternate between, for example, cutting, ablating and/or coagulation modes, each of which is characterized by specific set of heating parameters that are controlled from user-controlled elements situated on or around the handle 130. Other functionalities associated with the laser procedure may include sliding the scanning waveguide. The various actuation mechanisms described herein may act separately or simultaneously. Actuation may be performed using electrical, mechanical and/or an electro-mechanical mechanisms. Additional details regarding implementation of actuation mechanisms used in conjunction with an apparatus such as the apparatus 100 are provided, for example, in U.S. patent application Ser. No. 12/417,139, entitled "Tissue Treatment Device and Method," the content of which is hereby incorporated by reference in its entirety.

Optionally, in some embodiments, an additional feature that may be added is a component to prevent the laser energy from boring (drilling) through the tissue by adding a backstop at the distal end of the treatment tip. Because laser energy is powerful and non-divergent (and therefore does not attenuate significantly over large distances), situations where laser energy may penetrate through tissue adjacent to the tissue being treated could happen. This may cause accidental damage to non-targeted tissues. Having a backstop can thus significantly improve safety to the procedure performed by the device.

Alternatively, there may be situations where the laser energy should be allowed to freely travel (propagate) in space, e.g., when thick or bulky organs need to be cut. Combining the two requirements, the laser assisted apparatus may have, in some embodiments, a laser backstop which can be placed in or removed from the laser beam path according to an operator's needs. Thus, with reference to FIG. 2, schematic diagrams of a beam protector 200, mounted on a shaft 210, in the beam protector's ON and OFF modes, are shown. The shaft 210 may be similar to the supporting structure 110 depicted in FIG. 1. In some embodiments, the beam protector 200 includes a pivotable member 220 that pivots about an articulation point A with respect to the shaft 210 shown in FIG. 2. In the On mode, a distal section 230 of the member 220 pivots about the point A to form an optionally L-shaped member that blocks propagation of radiation emitted from the tip of the device. In the Off mode, the distal section 230 is in its second configuration such that the member 220 of the protector 200 substantially defines structure which enables free lasing towards the target tissue. The pivotable beam protectors may be implemented using foil pieces that are pivotably attached to each other at the point A. The pivoting member 210 is user controllable by some actuator (e.g., an actuator that is activated or controlled from the handle 130, as shown in FIG. 1).

Figure 3A:
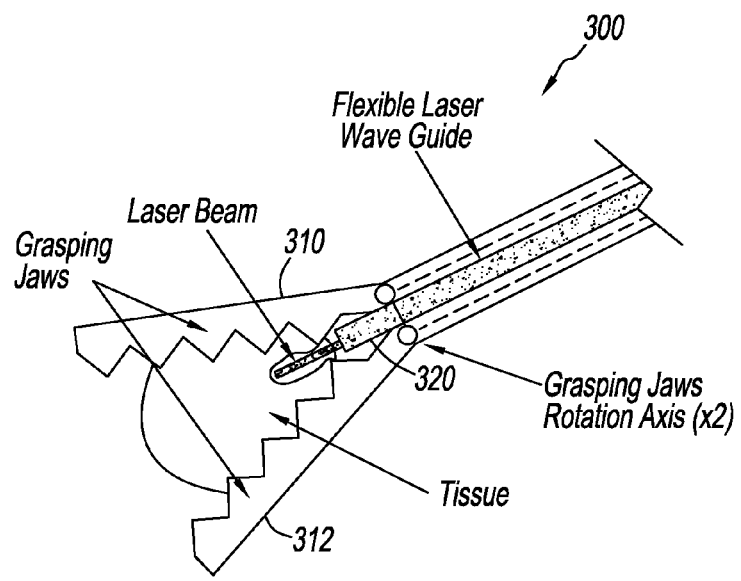
FIGS. 3a-c are schematic diagrams of implementations to direct laser radiation to tissue grasped by grasping tools.
Figure 3B:
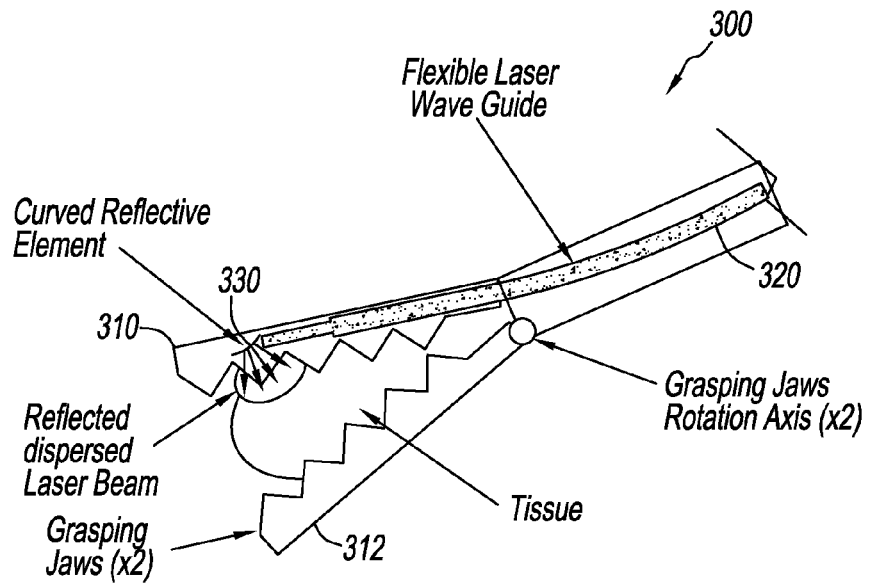
Figure 3C:
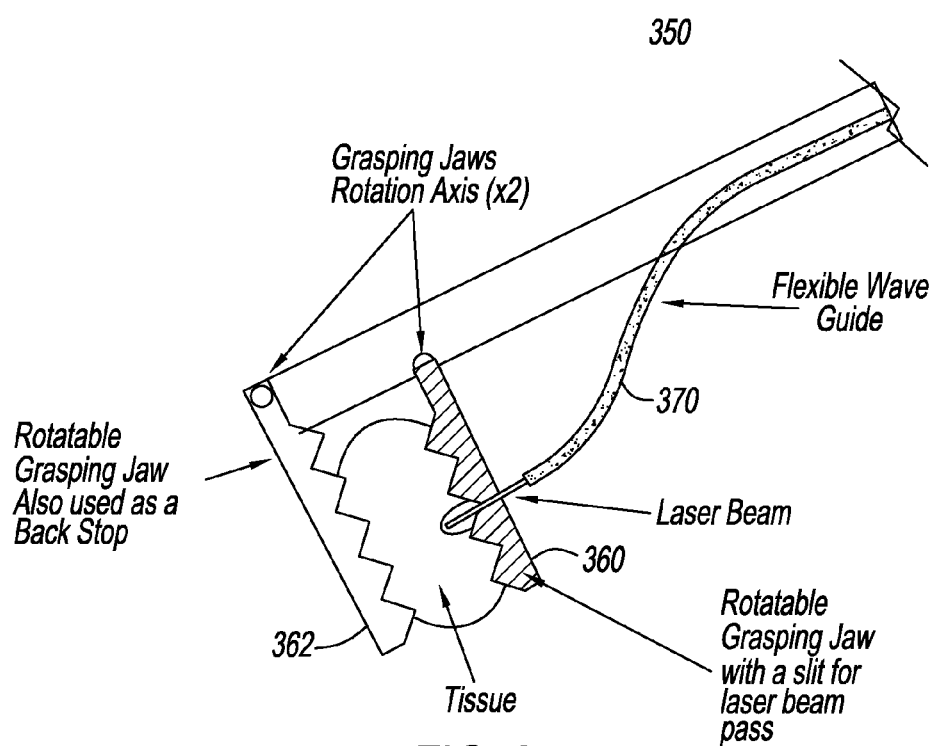

As noted, in some embodiments, the apparatus 100 and/or 200 may include a treatment tip, such as the treatment tips shown in FIGS. 3a-c, which include, for example, grasping tips (jaws). Implementation of such a feature in laser assisted apparatus (e.g., for laparoscopic surgery) is non-trivial because the laser energy often has to be directed at a direction that is substantially perpendicular to the longitudinal axis of the waveguide through which the laser energy is delivered (i.e., the plain defined by the tissue may be oriented in a substantially perpendicular direction to the longitudinal axis of the waveguide).

Referring to FIGS. 3a, 3b and 3c, schematic diagrams of implementations to direct laser radiation to tissue grasped by grasping tools/instruments (e.g., grasping jaws) are shown.

FIG. 3a depicts a laser assisted device 300 used, for example, for laparoscopic surgery, with grasping elements. After the tissue is grasped with, for example, jaws 310 and 312, a laser source (which may be similar to the laser source 150 depicted in FIG. 1) is activated and the generated beam is emitted from a flexible fiber 320 to achieve the desired effect on tissue, e.g., cutting or coagulating.

FIG. 3b depicts a grasping tool 300 similar to the grasping tool shown in FIG. 3a, except that in the implementation depicted in FIG. 3b a beam controller is used to cause the emitted radiation energy to be directed to hit the tissue from the side. This is achieved by using reflective element 330 as the beam controller, e.g., a curved (convex) mirror, which reflects the energy beam in the desired direction. In some embodiments, the surface of the reflector may be convex in one direction (e.g., the x-direction) and concave in another direction (e.g., the y-direction). By controlling the position and the angle of the reflective element (i.e., the beam controller of the implementations of FIG. 3b) with respect to the grasping jaw, the energy can be directed to hit the desired position at the required angle. It is to be noted that by using, for example, a reflective element, in some embodiments, a resultant divergent radiation emission is directed towards the tissue to thus irradiate a line (or an area) on the tissue and not just a single spot. Under these circumstances, the reflective surface acts not only to alter the direction of emission but to generate a divergent beam with a specific pre-determined spatial shape.

FIG. 3c depicts another implementation of a device 350 to enable irradiation of laser radiation directly on the grasped tissue. As shown, the grasping elements 360 and 362 do not pivot with respect to the tool shaft but rather move parallel to each other, a movement which enables grasping the tissue at substantially constant pressure all over the grasped tissue. In contrast, the grasping instruments depicted in FIGS. 3a and 3b result in pressure on the tissue being higher for the part closer to the pivoting pins and weaker in the distal parts of the grasping jaws. As further shown in FIG. 3c, the grasping jaws are placed perpendicular to the tool shaft, thus making it difficult to enter the abdominal cavity through a standard 5 mm trocar. Therefore, in some embodiments, the grasping jaws are configured to have a rotating pivoting functionality to enable them to lie flat (i.e., to be folded) with respect to the supporting structure (a tool shaft, tubular device, etc.) when inserted into the abdominal cavity through the trocar. During the procedure, the laser delivery waveguide 370 is placed perpendicularly to the tissue and the energy passes to the tissue through a slit or window in the jaw closer to the waveguide, whereas the remote jaw may serve as a backstop.

With reference again to FIG. 3a, in the depicted implementation the laser radiation hits the tissue at the same predefined position and practically "drills" through it. In the other depicted implementations, the laser radiation can be controlled to irradiate a line or an area on the tissue rather than a spot by either using a convex reflective element (as shown in FIG. 3b) or by generating a scanning movement of a flat mirror by moving a moveable reflective element back and forth as depicted, for example, in FIG. 4a, so that the tissue gets laser energy along a predefined path. Beam controlling to achieve this scanning pattern and distance is effected by the user controlling a special device or knob located on the handle, or can be done automatically using a processor-based device, configured to execute computer instructions, to perform a pre-defined and pre-stored scanning pattern.

Figure 4A:
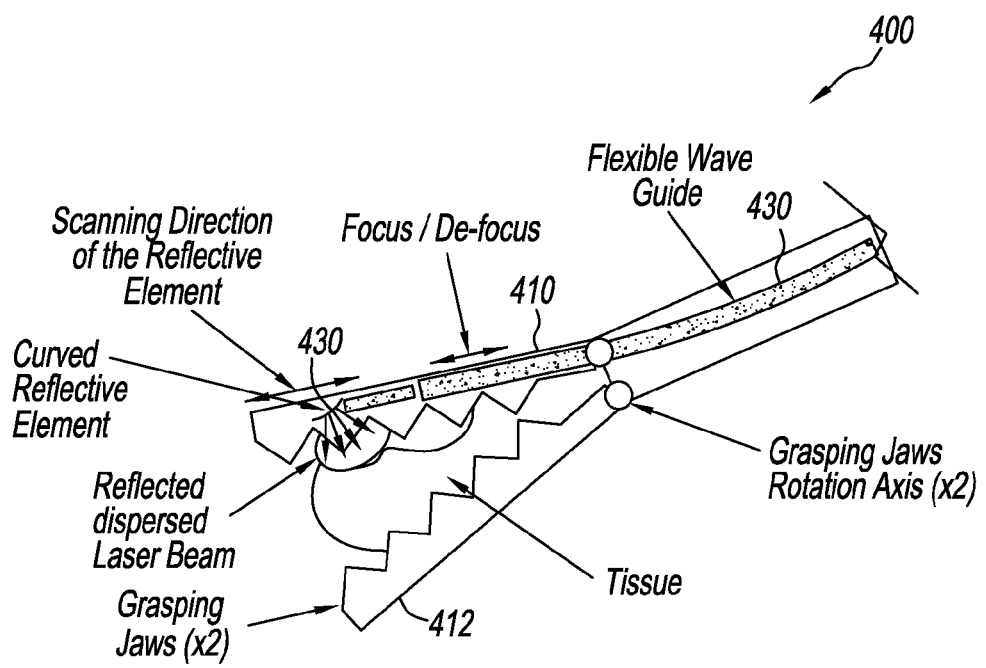
FIGS. 4a-b are schematic diagrams of additional implementations to direct laser radiation to tissue grasped by grasping tools.
Figure 4B:
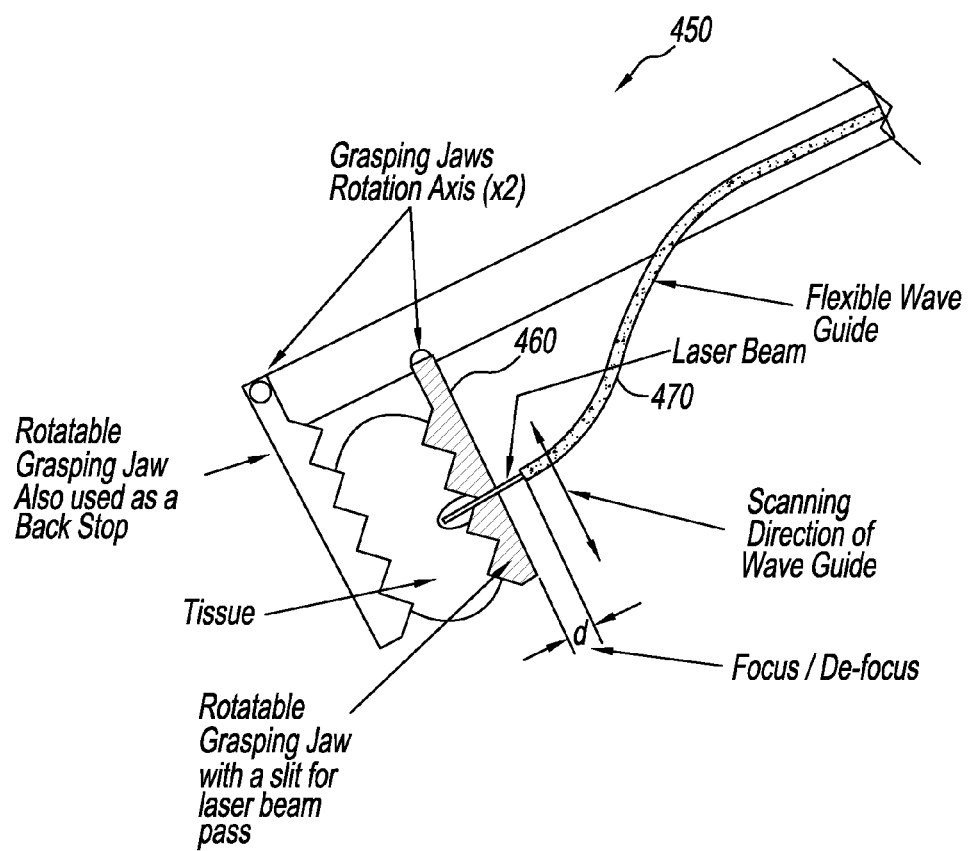

Referring to FIG. 4b, a schematic diagram of another treatment apparatus 450 that includes a grasping instrument is shown. In the implementation of the treatment device of FIG. 4b, beam control (to control tissue irradiation) is performed by moving a waveguide 470 up and down (i.e., in a scanning motion) as depicted in the schematic drawing, or alternatively, the fiber tip can be rotated around an axis perpendicular to the surface of the proximal grasping jaw 460. A beam controller implementing a scanning/moving mechanism may be used to control the scanning motion of the flexible waveguide. User-control of the scanning mechanism (e.g., to specify movement parameters) may be implemented through a user-control interface which may be located on the handle and operated by the user. In some embodiments, the scanning control mechanism may be implemented using a processor-based controller. A slit or a window in the proximal grasping member 460 (e.g., jaw) is used to enable passing the laser energy directly to the tissue while still grasping it in the exact location where, for example, the cut/coagulation are needed.

While the scanning movement depicted in FIG. 4b is substantially linear, in some embodiments, the flexible waveguide and/or the beam controller (also referred to as the scanning mechanism) controlling the motion of the waveguide are configured to cause spatial movements of the waveguide so that specific irradiation patterns or shapes can be applied to the tissue (e.g., to achieve specific cutting or coagulating patterns), including circular, rectangular or any other desired shape or pattern.

In some embodiments, the use of manual and/or automatic motorized scanning may be used to control the movement (linear and/or angular/radial) of the waveguides and/or components of the apparatus, as depicted in FIGS. 4a and 4b.

With continued reference to FIG. 4b, as understood, a laser beam is generally nearly non-divergent. When exiting a waveguide the laser beam has its minimal spot size and thus the highest area power density. Therefore, when the distance between the waveguide and the treated tissue increases, the power density is reduced. As the laser tissue interaction is influenced by the surface power density, controlling this distance enables the operator to better control the effect on the tissue. In some embodiments, increasing this distance can result in improved coagulation, whereas shortening it enhances cutting response. Accordingly, as depicted in FIG. 4b, the flexible waveguide can also be controlled (e.g., using a beam controller such as the beam controller 160 of FIG. 1) to be spatially displaced to increase or decrease the distance d between the distal end of the waveguide and the proximal grasping member. Control of the distance d enables alternating the focus and de-focus distances d to enable better control and overall performance. In some embodiments, the beam controller controlling the distance d between the distal end of the waveguide and the proximal grasping member may include actuators, such as controllable cords, strings, etc., coupled to the waveguide that can be user-controlled, for example, from a control handle of the apparatus (similar, for example, to the control handle 130 of the apparatus 100).

Figure 5A:
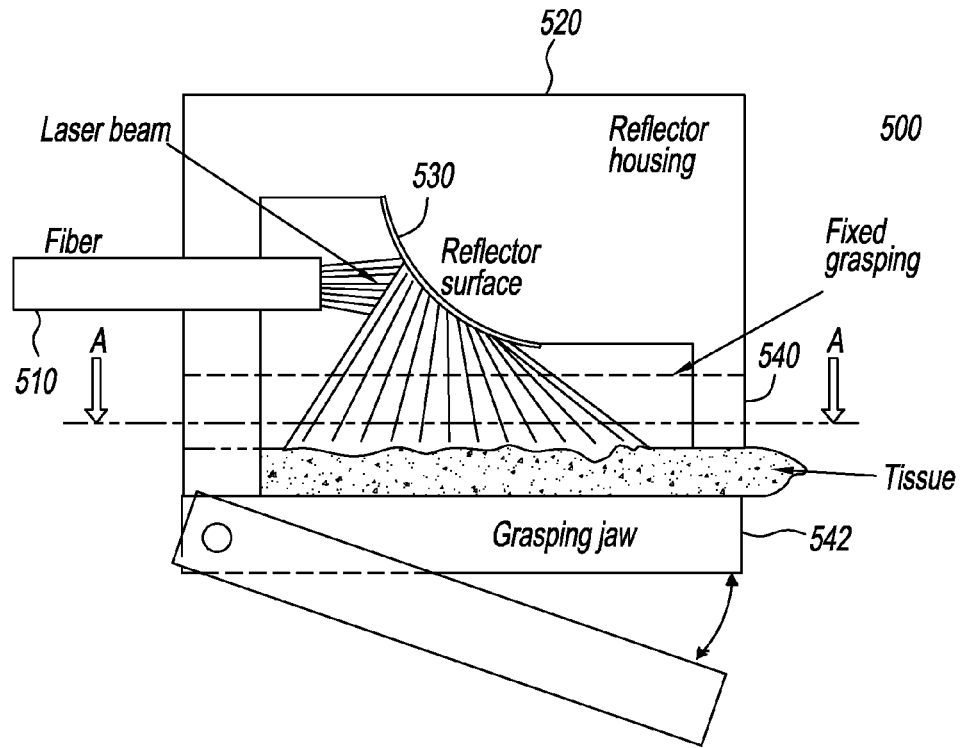
FIGS. 5*a-b* are schematic diagrams of a line cutter treatment device.
Figure 5B:
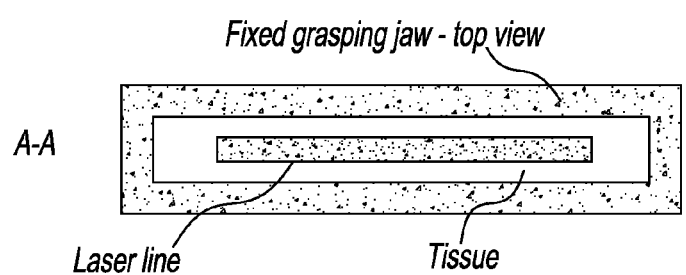
Figure 6:
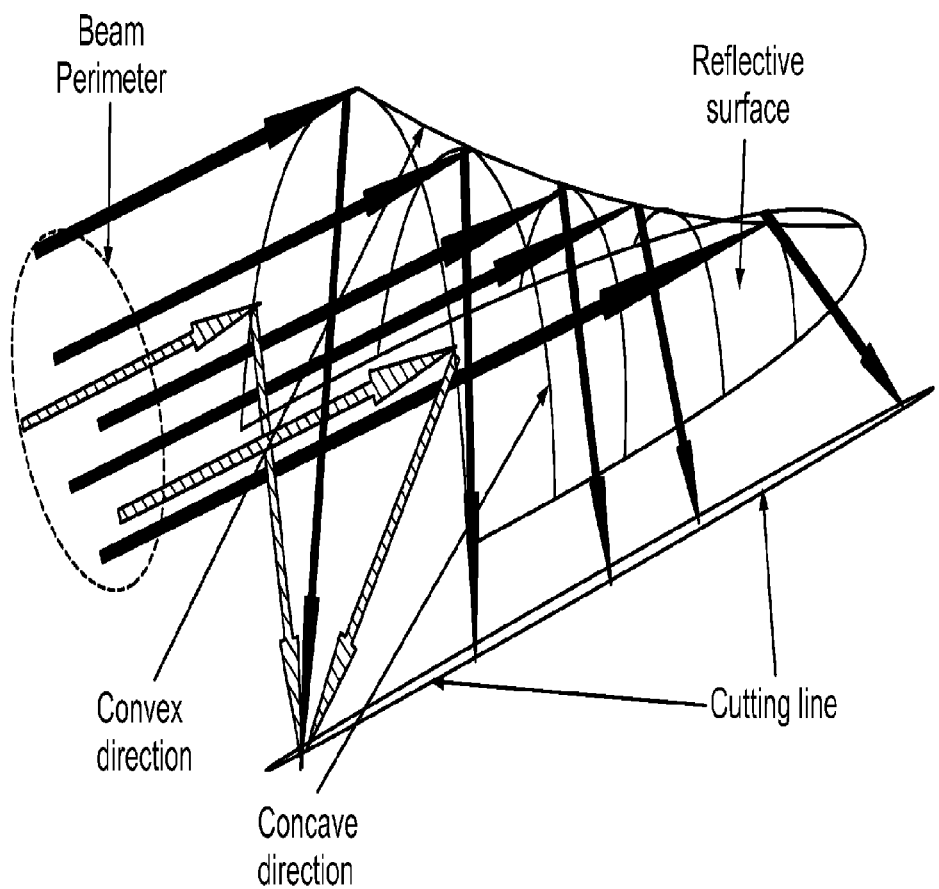
FIG. 6 is a diagram of an arrangement of a fiber and a reflector to direct radiation emitted by the fiber.

Referring to FIGS. 5-6, diagrams of a treatment apparatus that include a flexible laser waveguide and a beam controller are shown. The apparatus depicted in FIGS. 5-6 is one implementation of the embodiments described in relation to, for example, FIG. 3b. Specifically, and with reference to FIG. 5a, showing a schematic cross section side-view diagram of a distal end of a grasping line cutter (GLC) 500, the GLC is configured to cut tissue or blood vessels by grasping the tissue and manipulating or actuating the laser beam emitted from the fiber to irradiate an even line on the tissue, thus simultaneously forming an even cut over the targeted cutting area. Since the energy delivered by a GLC is the radiation emitted from a fiber 510, the tool (e.g., a laparoscopic tool) it connects to can be rigid or flexible. As shown in embodiment of the GLC illustrated in FIG. 5a, the GLC comprises the following parts:

1) A housing 520, which may be a rigid part, configured to perform the following functions: a) hold a waveguide (e.g., optical fiber) at a fixed position, and b) support a beam controller such as a reflector surface 530 positioned in front of the fiber 510. The reflector 530 is an optical component configured to distribute the laser beam into a substantially uniform line (as more particularly shown in FIG. 6). In general, the reflector surface's geometry can be adapted to perform various distributions of the laser beam, including, for example, diverging the beam in one dimension to form a line, converging the beam in another, optionally perpendicular direction to increase power density, etc. Thus, and as depicted in FIG. 6, in some embodiments, the reflector may define a substantially concave surface in one direction (e.g., in the transverse direction of the reflector shown in FIG. 6) and the reflector may further define a convex surface in another direction (e.g., along the longitudinal axis of the reflector of FIG. 6) to cause at least some other of the radiation reflected from the surface to be distributed substantially uniformly in a line extending in the other direction. Accordingly, the convex surface causes the spot shaped beam being emitted from the waveguide to diverge into a line which converges into a very narrow line by the concave surface. The reflector 530 may also be configured to compensate for non-uniform power distributions such as a Gaussian beam intensity distribution profile. The reflector 530 may also be configured to reduce the level of debris and dirt accumulation on the reflector by, for example, applying coating, directing purge gas through small holes in the reflector towards the tissue, etc. Purge gas coming out of the waveguide (e.g., in circumstances where the fiber is a hollow waveguide) prevents condensation of vapors from the tissue resulting from laser-tissue interaction.

2) A fixed grasping jaw 540. This component acts to provide contra force to the moving jaw (see below) in order to grasp tissue and hold it for cutting. With reference to FIG. 5b, showing a top view diagram of the fixed grasping jaw 540, in some embodiments, the fixed grasping jaw includes a window defined in the jaw to enable laser energy to pass through the jaw's window and reach the tissue. Generally, the window defined on the fixed jaw can be made from a transparent material, or, in some embodiments, can constitute an empty space area through which radiation (e.g., a laser beam) can pass.

3) A moving grasping jaw 542. The moving part of the line cutter can be placed against tissue when it is in the open position (so as to trap the tissue that is to be operated upon), and can grasp the tissue against the fixed grasping jaw when the moving jaw is in its closed position.

Figure 7A:
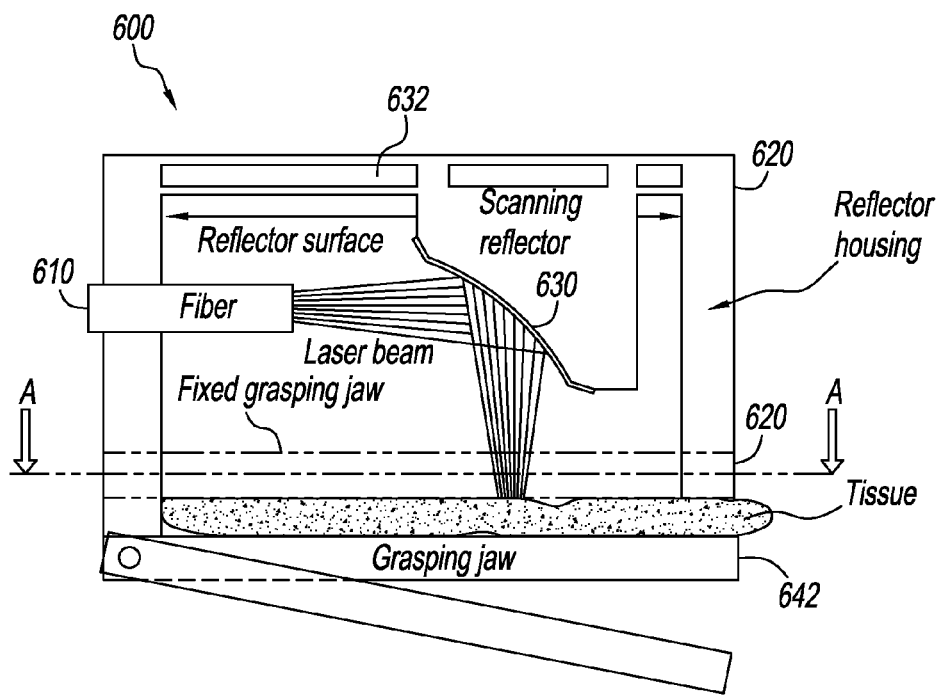
FIGS. 7*a-b* are schematic diagrams of a scanning cutter treatment device that includes a flexible laser waveguide.
Figure 7B:
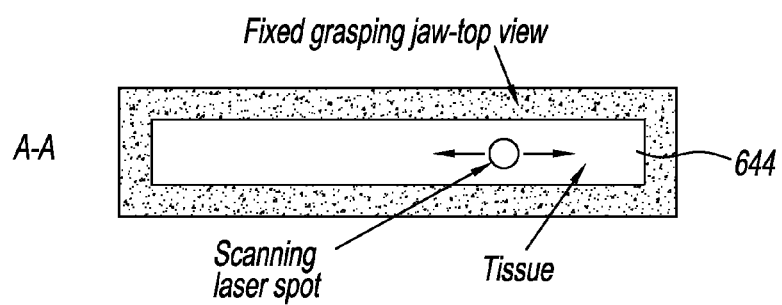

Referring to FIGS. 7a and 7b, schematic diagrams of a laser apparatus 600 (e.g., for use in laparoscopic procedures) including a flexible laser waveguide to perform laser irradiation using a beam controller (scanning mechanism) is shown. The laser apparatus 600, in this case a grasping scanning cutter (GSC), includes a distal end member (or tip) configured, for example, to cut tissue or blood vessels by grasping the tissue and manipulating (actuating) the laser beam emitted from a waveguide (e.g., a fiber) into a small area on the tissue, thus allowing for a full or partial cutting of the grasped tissue by causing the emitted laser beam to move across the targeted tissue (i.e., scanning the tissue). Laser radiation is thus emitted from a flexible fiber 610 connected to a rigid or flexible apparatus (e.g., laparoscopic apparatus). As shown in FIGS. 7a and 7b, in some embodiment, the GSC illustrated includes the following components:

1) A housing 620, possibly rigidly structured, to perform one or more of the following functions: a) hold a waveguide (e.g., an optical fiber) 610 at a fixed position, and b) provide a sliding guide for a traveling (moving) beam controller such as a scanning reflector 630 (i.e., a linear slide to cause the reflector 630 to move in a straight line).

2) A fixed grasping jaw 640. This element provides a contra force to a moving jaw 642 in order to grasp tissue and hold it for cutting. The fixed grasping jaw has, in some embodiments, a window 644 to allow the laser energy to reach the tissue (as shown in FIG. 7b). The window defined on the fixed jaw 640 can be made from a transparent material, or, in some embodiments, may constitute an empty space area through which radiation (e.g., laser radiation) can pass.

3) The moving (or traveling) scanning reflector 630 (i.e., the beam controller). This moveable element is configured to move inside a guide 632 (or track, channel, etc.) in the reflector housing 620, and has a reflecting surface positioned substantially in front of the waveguide 610. Scanning is achieved by controlling the movement of the reflector. The reflector is an optical component designed to distribute the laser beam into, for example, a small area on the tissue (see FIG. 7b). In general, the reflector surface geometry can be structured to perform various distributions of the laser beam. For example, the reflector surface can be structured to converge the laser beam to increase power density. The reflector can also be adapted to compensate for non-uniform power distributions (e.g., power distribution having a Gaussian profile). The reflector can be configured to reduce debris and dirt accumulation on the reflector by, for example, applying coating, directing purge gas through small holes in the reflector, etc. Purge gas emerging, in some embodiments, from a hollow waveguide, prevents deposits of vapors, smoke and tissue debris resulting from the laser-tissue interaction on the inner surface of the waveguide in its distal tip and the front surface of the waveguide. In some embodiments, the distance between the distal end of the fiber 610 and the reflector 630 can be controlled to thus control the focus/de-focus operability of the device, which also enables controlling the power density of the radiation energy.

4) The moving grasping jaw 642. The moving grasping part enables tissue to be placed against the jaw when the jaw is in its open position (relative to the fixed jaw). When placed against the moving jaw in the jaw's open position, the tissue to be treated is effectively trapped. When the moving jaw is actuated (moved) to its closed position (relative to the fixed jaw) the tissue is grasped by the moving and fixed jaws. In some embodiments, the apparatus 600 can be implemented with parallel grasping members configured to be displaced relative to each other in a manner similar to that described in relation to the embodiments, for example, of FIG. 4b.

In some implementations, the beam controller used, for example, in the implementations of FIGS. 5 and 7 may be a curved spatial reflector having a pre-determined geometry. The curved spatial reflector may be configured to direct the radiation emitted from the distal end of the flexible waveguide so that the directed radiation is substantially distributed over a section in the target tissue according to a pre-determined cutting geometry resulting from the pre-determined geometry of the curved spatial reflector. In some variations, the resulting shape may be similar to one of an ellipse or a rectangle, with one axis of the ellipse or rectangle having narrow dimensions such that a resulting cut in the tissue is substantially a thin line.

As described herein, in some implementations, application of energy to the target area (the target tissue) in a scanning pattern may be performed by controlling a slideable scanning tip (e.g. a silver tip) coupleable to a waveguide to move the emitting end of the scanning tip to apply radiation to the target tissue in a scanning pattern. The sliding tip may be, in effect, a waveguide, coupled to the main waveguide, and may have a bent shape near its emitting end to direct the beam towards the tissue. In some embodiments, instead of using a sliding tip and actuating it to displace the tip in a controlled manner, the main waveguide (i.e., the waveguide coupled to the laser source) may be controllably displaceable and have a bent distal end such that upon actuation of the main waveguide to displace it, the bent distal end is controllably moved to cause radiation to be applied to the target tissue in a scanning pattern.

Thus, for example, in some embodiments, a beam controller to control the direction of the beam (e.g., in relation to, for example, the apparatus 100, 500 and 600) includes a controllably displaceable scanning tip coupled to the waveguide, and an actuator to actuate a section of the scanning tip. The actuation of the scanning tip causes the tip to be controllably displaced to apply radiation energy, delivered via the waveguide, to different locations of a target tissue in a scanning pattern. In some embodiments, the waveguide may include the scanning tip (i.e., the scanning tip is not a separate element that is coupled to the waveguide, but is rather, in such embodiment, the distal end of the waveguide). In some embodiments, the actuation of the scanning tip causing the tip to be controllably displaced can cause one or more of, for example, controllable linear displacement and/or controllable radial displacement of the scanning tip over an angular range.

Figure 8:
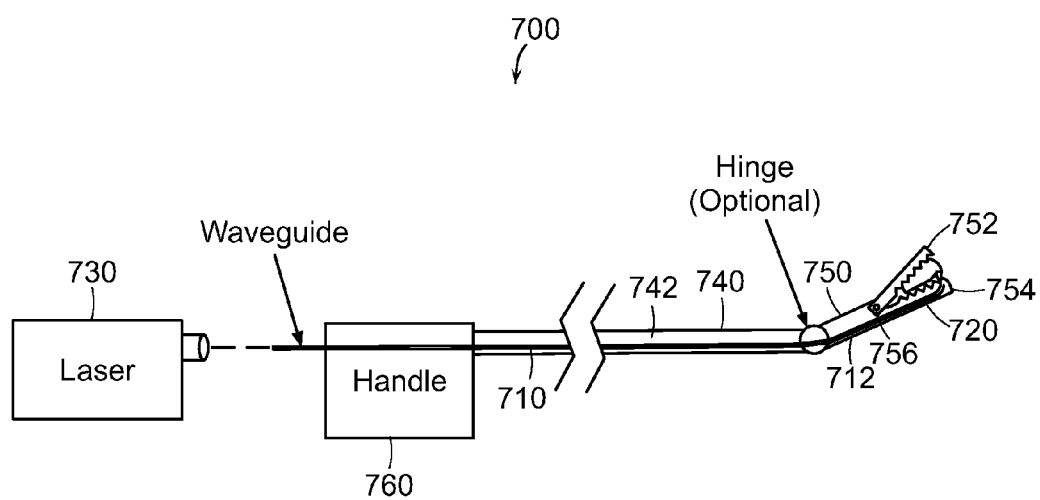
FIG. 8 is a cross-section schematic diagram of an apparatus that includes a controllably displaceable optionally scanning treatment tip.

With reference now to FIG. 8, a cross-section schematic diagram of an apparatus 700 is shown. The apparatus 700 includes a waveguide 710 coupled, e.g., at its distal end, to controllably displaceable scanning tip 720 (also referred to as a distal tip or a scanning waveguide) such that controlled actuation of the scanning tip 720 causes controlled displacement of the scanning tip 720. The scanning tip may be, in some embodiments, a hollow tube or cylinder that is coupleable to the waveguide 710 at one of its open ends (e.g., the distal end of the waveguide 710 may be, at least partly, received within the hollow tube), and may have a bent emitting end that faces the tissue to be treated (i.e., radiation emitted from that emitting end of the scanning tip would be directed towards the target tissue). The scanning tip 720 may be constructed from, for example, conducting materials (e.g., silver, or some other conducting metal) suitable to direct radiation energy from the distal end of the waveguide 710 to the emitting end of the scanning tip. The scanning tip 720 may have a generally constant inner diameter but may be tapered with the exit diameter being smaller than the entrance diameter to improve the beam concentricity as it hits the tissue. In some implementations, the scanning tip may be a waveguide, such as a laser fiber or other suitable waveguides, that are separate from the waveguide 710. Under those circumstances, the scanning tip 720 may be coupled to the waveguide 710 by, for example, splicing, by using suitable waveguide couplers, etc. In some embodiments, the scanning tip 720 may be part of the waveguide 710 (i.e., the distal end of the waveguide 710 is the scanning tip 720) which is bent to the required angle.

The scanning tip 720 is controllably displaceable such that upon actuation of the scanning tip 720, the scanning tip is displaced, e.g., linearly or radially, such that radiation emitted from the tip's distal end is applied to different locations of the target tissue. The scanning tip 720 is thus configured to implement a scanning waveguide. As will be described in greater details below, in some embodiments, radial displacement of the tip can be controlled to cause the tip to be radially displaced over a radial range. In some implementations, the tip may be controllably displaced over an angular range of, for example, 0-180°, and in some embodiments, over an angular range of 20°-160°. The angular range refers to the angle formed between the scanning tip 720 and another portion of the waveguide 710, for example, the portion 712 shown in FIG. 8.

The waveguide 710 is configured to direct radiation from a radiation source 730, which may be similar to the radiation source used, for example, in the implementation depicted in FIG. 1, e.g., a CO2 laser system generating radiation having a typical wavelength of approximately 10.6 µm, that is coupled to one end of the waveguide 710. Other possible laser systems include, for example, an Er:YAG laser system (that typically operates to generate radiation having a wavelength of approximately 2.94 µm), a Ho:YAG laser system (used, for example, for urological applications) typically operating to generate a wavelength having a wavelength of approximately 2.1 µm and/or Nd:YAG laser system emitting radiation having a wavelength of approximately 1.06 µm. Other suitable laser devices may include, in some embodiments, at least one laser diode (which may be arranged in a diode array). The at least one laser diode may include a quantum-well laser based on Antimonide (Sb) compounds such as, for example, In(Al) GaAsSb-based compounds, GaSb-based compounds, etc. In some embodiments, the first radiation source may include a specially doped fiber laser such as, for example, erbium-doped fluorozirconate fibre laser. Other types of radiation sources may also be used.

The radiation from the radiation source may be coupled using, for example, a connector (e.g., a CO2 laser connector). Suitable laser connectors to connect the laser generating device to the waveguide (or conduit) may include, for example, laser SMA connectors, laser S-T connectors, etc. Other coupling mechanisms (e.g., based on arrangements of optical elements) may also be used. The radiation coupled to the waveguide 710 is transmitted through the waveguide and emitted from a distal emitting end 722 (shown in FIGS. 9a-b) at the scanning tip 720 of the waveguide onto a target tissue (e.g., human tissue).

The type and/or configuration of the waveguide 710 to deliver the radiation generated by the radiation source 730 may be based, at least in part, on the particular radiation source used. For example, in circumstances in which the first radiation source is a CO2 laser device, the waveguide 710 may be a hollow waveguide adapted to direct radiation generated by a CO2 laser device. Other possible waveguides that may be used include waveguides to transmit optical radiation having such wavelength includes, for example, glass or crystalline fibers, Sapphire fibers, Germanate glass fibers, a combination of Germanate glass fibers with Sapphire tip, hollow core fibers and/or any other suitable waveguides or radiation conduits to deliver laser energy.

As further shown in FIG. 8, the apparatus 700 includes a supporting structure 740 coupled at its distal end to a treatment tip (such as a grasping tool) 750. The supporting structure may be similar to the supporting structure 110 of the apparatus 100 of FIG. 1, and may be, in some implementations, a shaft, a tubular-based device such as a scope-based device, e.g., a laparoscope, an endoscope, etc. In the embodiments of FIG. 8, the waveguide 710 is received within an inner volume 742 defined by the supporting structure 740. In some embodiments, the supporting structure 740 is optionally bent at a hinge 746, and thus the waveguide 710 received within the inner volume defined by the supporting structure 740 is likewise bent and passes through the hinge. Use of the hinge is generally associated with use of single port surgery which is becoming common in the MIS market.

The treatment tip 750 includes, in some embodiments, an inner channel that is in communication with the inner volume 742 defined in the supporting structure 740 and extends to an opening defined in an external surface of the treatment tip. The inner channel is structured to receive at least a portion of the waveguide 710 and the scanning tip 720 coupled to the waveguide 710. As noted, in some embodiments, the waveguide 710 includes the scanning tip 720 such that the scanning tip is part of the waveguide itself The grasping tool 750 coupled to the supporting structure 740 may include, in some implementations, one or more members, such as closeable jaws 752 and 754 having contacting surfaces to contact the target tissue and facilitate performance of the implemented operations on the target tissue. The contacting surfaces of the jaws 752 and 754 may have an irregular structure (e.g., a roughened or jugged surface) to enable improved traction with the target tissue that is to come in contact with the contacting surfaces. In some implementations, closeable jaws with embedded heating elements, such as the closeable jaws described in U.S. patent application Ser. No. 12/417,139, entitled "Tissue Treatment Device and Method". In some embodiments, at least one of the jaws, e.g., jaw 752, may be a pivotable jaw that can pivot (rotate) about a pivoting point 756. In some embodiments, at least one of the jaws, e.g., a jaw 754, may be fixed (e.g., relative to the supporting structure 740). In such implementations, the grasping operations are performed using only one rotating jaw, namely, the jaw 752. Such implementations can generally reduce the extent of the bending of the waveguide. In some implementations, both closeable jaws 752 and 754 may be rotateable.

The apparatus 700 further includes a user-actuated handle 760 through which operations of the apparatus 700, including the treatment tip 750, may be controlled. The handle 760 may enable control of the device's various functionalities, including such functionalities as the activation of the grasper (implemented, for example, using the closeable jaws 752 and 754), controlling the movement and orientation of the apparatus, e.g., controlling rotation of around the axial rod of the apparatus, controlling the displacement of the flexible waveguide and/or of the scanning tip 720, etc. In some embodiments, the handle 760 may comprise several individual user-controllable elements such as, for example, levers, buttons, knobs, and other types of user controllable elements. Such user-controllable elements may be arranged on the apparatus 700, for example, on the handle 760. In response to user manipulation of any one of the user controllable elements, the actuation mechanisms controlled via the one or more user-controllable elements are actuated, thus causing an associated movement or manipulation of the treatment tip, the supporting structure 740, the waveguide 710, the scanning tip 720, and any other element of the apparatus 700. Another user-controllable interfacing element could be an ON-OFF button which controls delivery of laser radiation via the waveguide 710 at the operator's discretion. Another control button can alternate between cutting, ablating and/or coagulation modes, each of which is characterized by specific set of heating parameters that are controlled from user-controlled elements situated on or around the handle 760. Other functionalities are associated with the laser laparoscopy and include sliding the scanning tip and optionally activating the laser beam. The various actuation mechanisms described herein may act separately or simultaneously. Additional details regarding implementation of actuation mechanisms used in conjunction with a device such as the device 700 are provided, for example, in U.S. patent application Ser. No. 12/417,139, entitled "Tissue Treatment Device and Method."

Figure 9A:
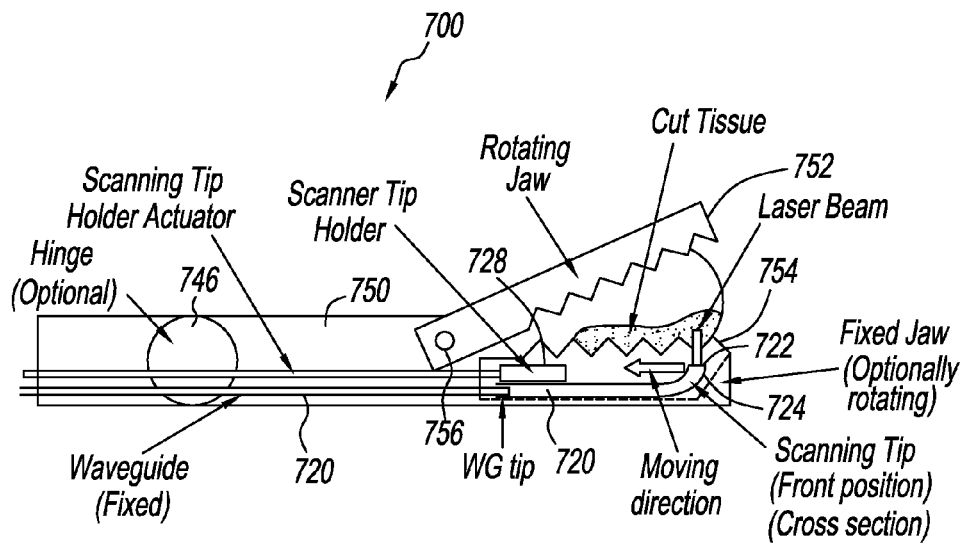
FIGS. 9*a-b* is a magnified schematic view of the treatment tip of FIG. 12, with the scanning tip located in its front and back positions, respectively.
Figure 9B:
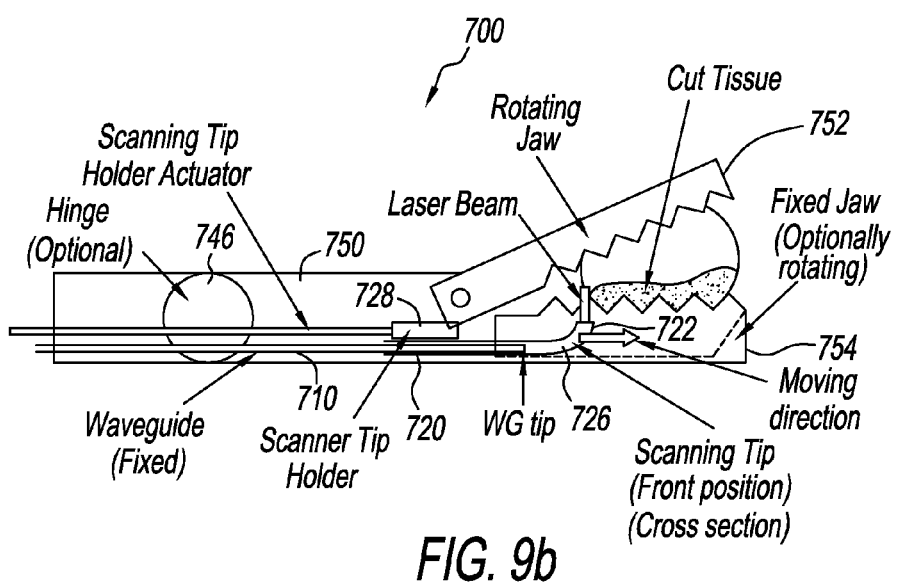

With reference to FIG. 9*a*, a magnified schematic view of the distal portion of the apparatus 700 of FIG. 8 is shown. The scanning tip 720 may be displaced from a front position 724 to a back position 726 (shown in FIG. 9*b*) by actuating the scanning tip using the holder 728. In implementations in which the scanning tip is a hollow element that is separate from the flexible waveguide 710, displacement of the scanning tip 720 results in the sliding of the scanning tip 720 along the end portion of the waveguide 710. That is, as the scanning tip 720 moves from the front position 724 to the back position 726, more of the distal portion of the waveguide 710 is received within the inner volume of the scanning tip 720.

As the scanning tip 720 is displaced, the tip's emitting end 722 is also displaced linearly relative to the target tissue, and as a result, radiation emitted from the emitting end 722 is applied to different locations of the target tissue. The controlled application of radiation to different locations of the tissue thus results in scanned pattern radiation emissions.

In implementations in which the scanning tip is part of the waveguide 710, it is the waveguide 710 itself that is displaced to, for example, move it linearly to cause radiation to be applied to the target tissue in a scanned pattern. In such implementations, the distal end of the waveguide 710 is bent so that radiation emitted from the waveguide's distal end is directed towards the tissue.

In some embodiments, actuation of the scanning tip 720 is performed by a holder 728 (also referred to as a scanning tip holder and/or as an actuator) that includes a displaceable block in mechanical communication with the scanning tip 720. The holder 728 is mechanically actuated using an actuation mechanism controlled, for example, through a user-controlled element located at the handle 760. In some embodiments, the actuation mechanism (e.g., strings to push or pull the holder 728) passes through the hinge, the treatment tip and/or the hollow waveguide itself (e.g., in implementations in which the waveguide is a hollow waveguide configured to deliver radiation generated by a CO2 laser). Other configurations for connecting the actuation mechanism to the holder may also be used.

Figure 10:
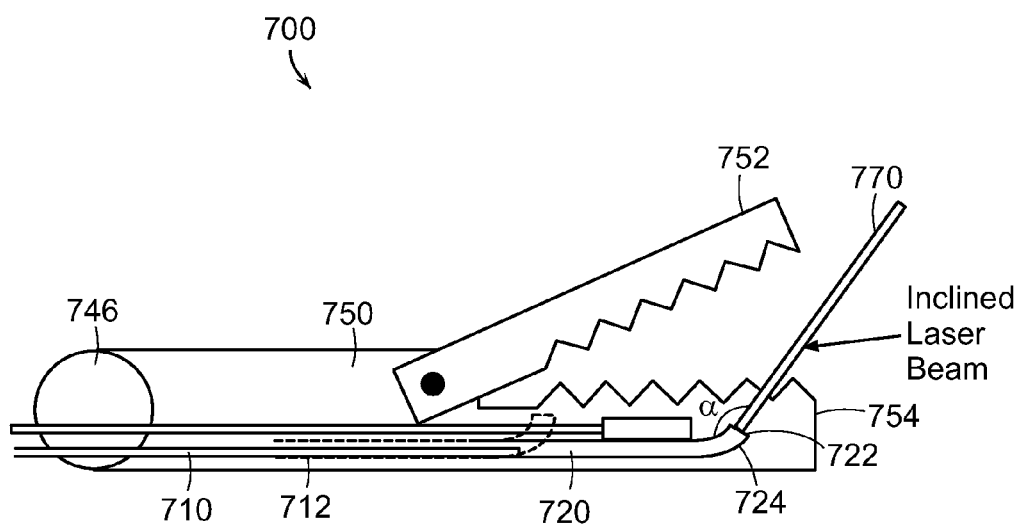
FIG. 10 is a schematic diagram of another implementation of an apparatus with a controllably displaceable scanning tip.

With reference to FIG. 10, in some embodiments, the bent portion of the scanning tip may form an angle, relative to, for example, the fixed jaw, that is different from substantially 90°. For example, the bent portion proximate the emitting end of the scanning tip may form an angle α, relative to the surface of the fixed jaw, e.g. about 110°, depending on the instrument structure. Having the resultant beam emitted from the bent emitting end hitting the tissue at some particular angle α enables energy, in some cases, to be emitted outside of the treatment tip without having the rotating jaw 752 functioning as a back stop. This configuration has the advantage of enabling the operator to use the apparatus for direct firing when needed.

In some variations, the extent of the bending radius of the scanning tip can be controlled. Having a relatively high bending radius may reduce the heat load but will result in a smaller angular range (and may also result in the laser beam angle higher than 90°). In some implementations, some compromise between the angle at which the beam hits the tissue and the transmission of the energy may be required because the energy transmission tends to decrease with the radius of curvature of the scanning waveguide.

As noted, in some implementations, the waveguide 710 and/or the scanning tip 720 may be radially displaceable. For example, in implementations where the waveguide 710 includes the scanning tip 720 (i.e., the scanning tip is not a separate element from the waveguide), a part of the distal portion of the waveguide may be stationary, with at least part of the distal portion being bent and free to rotate above a fixed pivoting point. In response to actuation of the actuator controlling the radial movement of the distal portion proximate the emitting end of the waveguide, the emitting end may be radially displaced to thus apply radiation emitted from its end in a scanned pattern.

In some embodiments, the holder 728 actuating to the scanning tip may also be used as a heat sink to absorb heat created inside the waveguide.

In some implementations, the apparatus 700 may be fitted into a supporting structure, such as a shaft or a tubular device such as a scope-based instrument, configured to direct the apparatus to an area to be treated and to enable the apparatus (e.g., the waveguide 710, the scanning tip 720 and/or the treatment tip 750) to be operated. Thus, as described in relation to the apparatus 100 of FIG. 1, in some embodiments, the supporting structure may be a regular stand-alone tube or shaft, a duodenoscope, bronchoscope, urethroscope, etc.

Figure 11:
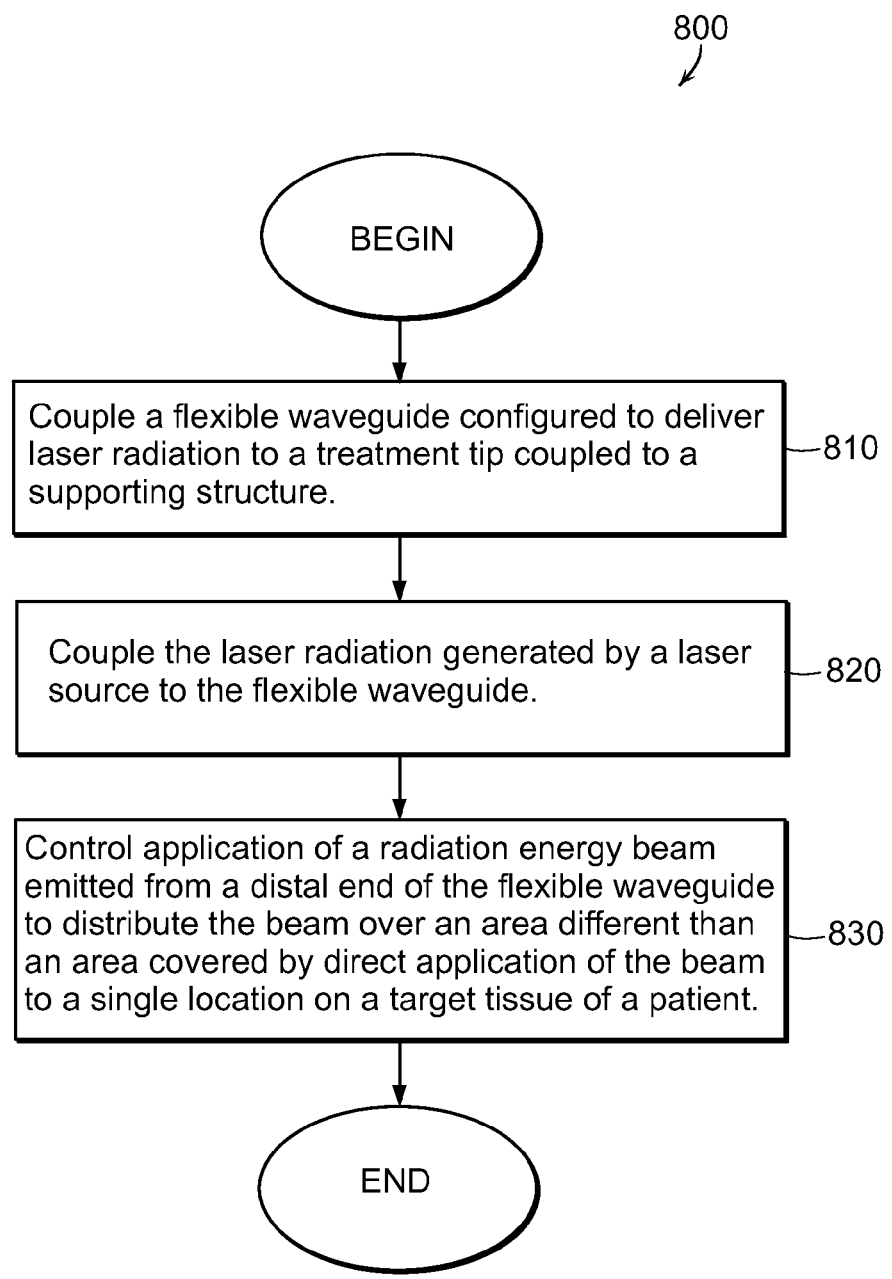
FIG. 11 is a flowchart of a procedure using a controllably displaceable scanning tip.

With reference to FIG. 11 a flowchart of a procedure 800 is shown. Initially, a waveguide, such as the waveguide 110 shown in FIG. 1 (or any of the other waveguides of FIGS. 2-10), is coupled 810 to a treatment tip that is coupled to a supporting structure (e.g., a shaft, a tubular device such as a regular tube or a scope-based device, etc.). The waveguide may be coupled to the treatment tip (such as a grasper) in such a way that the distal end of the waveguide is coupled to the treatment tip. In some embodiments, the treatment tip may be part of the supporting structure. In some embodiments, the waveguide may be integrated into the treatment tip. In some implementations, the waveguide may need to be coupled just once, either to the treatment tip or the supporting structure, because the treatment tip and supporting structure may already be coupled to each other. Put another way, in some implementations, the waveguide may be coupled to a treatment instrument which is composed of a supporting structure and a treatment tip. The waveguide can be coupled to either one or both of the supporting structure and treatment tip (instrument). In some embodiments, the waveguide may be coupled separately to both the supporting structure and the treatment tip.

Laser radiation from a laser source (such as the laser source 150 depicted in FIG. 1) is then coupled 820 into the waveguide and delivered to the waveguide's emitting end.

Application of a radiation energy beam, emitted from the emitting end of the waveguide onto target tissue of a patient is controlled 830 such that the emitted beam is distributed over an area different from an area covered by direct application of the beam to a single location on the target tissue (i.e., the area that would have been covered without controlling the locations where the beam is applied). Controlling the application of the beam onto the target tissue can be performed using, for example, one or more of the beam controllers described herein, including, a beam controller to control the spatial movement of the waveguide, a beam controller based on a reflector to direct to the target tissue the beam applied from the emitting end to the reflector, a beam controller for controllably displacing a scanning tip (e.g., a hollow tip that receives the waveguide) to cause the beam to be directed to different locations of the tissue, etc.

As mentioned above, flexibility of a waveguide and/or devices using waveguides is important for performing MIS.

Many new tools are developed for use in single port surgical procedures and also for use in NOTES and robotic surgical procedures.

The use of waveguide can significantly contribute to the development and implementation of flexible surgical apparatus, such as flexible laparoscopic apparatus and devices. The embodiments described in relation to FIGS. 1-10 can be implemented using different types of supporting structures, including tubular device (e.g., tubes, scope-based devices, etc.), rigid structures (e.g., a shaft), etc. The supporting structures may be configured to, in addition to enabling operation of rotateable jaws, also provide the jaws additional degrees of freedom relative to other axes. For example, rotateable jaws and/or the supporting structures to which the jaws are coupled, may be manipulated to be displaced relative to other axes, e.g., rotate phi ($\phi$) degrees and/or theta ($\theta$) degrees with respect to two other axes. To control the rotation of the tip (e.g., a tip including grasping jaws) relative to a number of axes, a joint, which may be located about 20-50 mm behind the tip of the tool, may be used. This joint may enable passing a laser waveguide inside the joint and, therefore, using the laser waveguide in these tools has an advantage when compared to the ultrasound based tools which require a straight shaft to deliver the ultrasound energy to the tip.

The above mentioned use of laser waveguides enables passing them through working channels of, for example, endoscopes of various sizes. Such endoscopes can be either rigid or flexible. Generally, the endoscope, which includes a viewing system, once it reaches the target tissue at which the treatment device can be deployed, the laser treatment device is extended from the exit end of the working channel. At this point the laser waveguide, or a device into which the waveguide is integrated can be directed, using controls, to any required point which needs to be cut, coagulated or otherwise operated upon.

In some embodiments, an aiming beam which is directed through the waveguide and which is used to indicate the point on the tissue where the laser beam is going to be applied, may be used. The aiming beam can be implemented as any light with a wavelength in the visible range, typically, but not limited to, red light having a wavelength of 635 nm or green at 532 nm. The use of such aiming beam is mainly intended to increase safety of procedures performed in which pre-viewing of the target to be treated can prevent mistakes from occurring due to lack of depth of field visibility when essentially 2D viewing tools, such as endoscopes or laparoscopes, are used. Directing (or passing) of the visible aiming beam is easier to implement in solid waveguides or fiber optics due to the material properties of these fibers, which are usually made of silica. However, in infrared waveguides, e.g. those used to deliver energy for the "ideal scalpel" CO2 laser system or for Erbium-YAG lasers, passing the aiming beam becomes a challenge. Implementations of aiming mechanisms for use with, for example, hollow waveguides configured to deliver infrared radiation are described for example, in U.S. patent application Ser. No. 12/564,325, entitled "Waveguides with Aiming Mechanisms" and filed Sep. 22, 2009, the content of which is hereby incorporated by reference in its entirety.

As tissue tends to stick onto heated surfaces of device for laparoscopic surgery, there arises the need to prevent such occurrences, or at least to enable cleaning of any residue produced during a procedure. Thus, a laser assisted device for various procedures can further include a cleaning device which helps remove tissue residues which may accumulate on the grasping jaws. In some embodiments, another possible implementation to address the problem of residue is to add "non stick", e.g., Teflon-based, coating to the grasping members (grasping jaws) and/or to any other surface used in the treatment device, including reflectors, beam protectors, etc., which may be in contact with the tissue. In some embodiments, another option that may be implemented is to provide steady flow of some liquid/gas which may prevent, at least to some extent, tissue residue accumulation of any of the above-mentioned surfaces. Such purge gases, for example, CO2 gas which is used to insufflate the abdominal cavity during various procedures, can pass either through a hollow waveguide (i.e., if a hollow waveguide is used to deliver laser radiation) or through a separate channel. A description of an implementation of a purge gas mechanism is provided, for example, in U.S. patent application Ser. No. 12/564,325. Letting $CO_2$ gas to pass through the hollow waveguide would require, however, use of laser wavelengths different from 10.6 μm which characterizes common $CO_2$ lasers. Particularly, in situations where a laser beam passes in the same or similar media to that by which the laser beam was created (CO2 gas in this example), the laser beam's power would be rapidly attenuated (e.g., due to the so-called "thermal blooming effect"). Accordingly, in some implementations, one option would be to use a laser system based on an isotope of $CO_2$, e.g., a $^{13}CO2$ laser system that generates radiation having a wavelength of 11.2 μm.

As noted, the laser assisted device for various procedures delivers energy produced in some laser energy source. Such systems may include any desired laser at any desired wavelength. Although the CO2 laser system is considered to be a suitable for various applications (e.g., laparoscopic applications), apparatus, devices and methods described herein are not restricted to any specific type of laser or wavelength.

In some embodiments, characteristics and behavior of the energy source may be controlled, including such characteristics as the average power, energy per pulse, frequency, specific shape of pulses, etc. Some or all of these characteristics may be controlled based on specification and inputs provided by the user. A control interface for the laser source to enable user control of the laser source enables the user to optimize the laser performance in terms of cutting/coagulating (or performing any other operation), especially given that different organs or tissue types require different settings for optimal effect. Control of the characteristics of the radiation applied to the target tissue may also be effectuated by controlling other elements of the apparatus, e.g., adding filtering elements to the apparatus to control radiation delivery, controlling the waveguide, etc.

The user may also define a range of energy or any other parameter using the user interface of the laser source system.

In some embodiments, several tools can be energized by one laser source. This option may require alternating between the various laser assisted apparatus which can be manually controlled (e.g., by some foot switch) or, alternatively, can be switched when the ON-OFF button is activated on each apparatus' individual handle.

A laser assisted apparatus can, in some embodiments, be configured to control the various required movements of the tool tip. For example, controlling the operation of the tool tip may include maneuvering the tip in space, activating the focus and de-focus functionality, spatially moving the tip along the various axes where rotation or linear movements are possible, etc. Optionally, an ON-OFF trigger as well as a control switch to alternate between cutting, coagulating and other types of operations, may also be included. These controls can also be implemented using a foot-switch activated by the operator's foot or may be hand-actuated.

In some embodiments, the tip of the laser assisted apparatus can include other mechanisms to better control the apparatus performance. For example, these mechanisms may include sensing or measuring devices such as, but not limited to, temperature sensors to measure the temperature, impedance sensors and/or sensors (or meters) to monitor the level of delivered energy. Such sensors/measurement mechanisms can be used to provide the operator with information to indicate, for example, if the desired effect has been achieved, e.g., by a specific tone emitted from the device or by activating a closed loop control which stops energy delivery even if the operator keeps activating the device. The data from such sensors may be delivered to, for example, a processor-based computing device which can be used to control laser energy delivery. Such a controller, in turn, may reduce the possibility of applying excess energy to specific tissue or causing excessive heating of the reflector (or any element of the device), and can give the operator indication of the temperature the tissue has reached (e.g., by measuring its impedance).

Thermal Protection Instrument using a Beam Blocking Element

Figure 2:
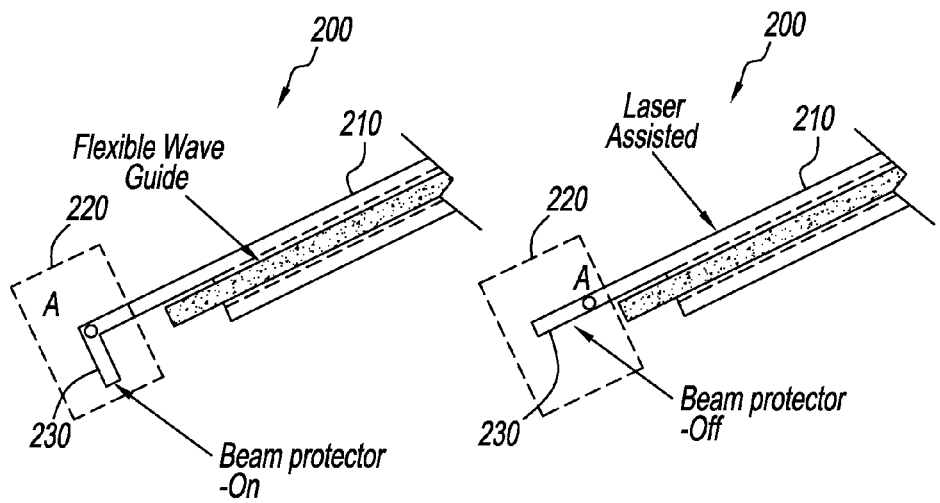
FIG. 2 are schematic diagrams of beam protectors in their On and Off modes.

As described herein, in some embodiments, laser energized apparatus/tools may include mechanism, such as backstops, to prevent energy not absorbed by the target tissue from further propagating (see, for example, the implementations depicted in FIG. 2).

In some embodiments, a thermal protection instrument, which may serve as a backstop, is used to contact the tissue and to be moved along the treated tissue while cutting it (such an arrangement is generally used for thin tissue layers dissection). As will be described in greater details below, in some embodiments, a thermal protection instrument may serve as a grasping member (also referred to as a jaw) positioned opposite an energy emitting member in grasper-device implementations in which an energy emitting mechanism (e.g., an emitting end of a waveguide) is positioned proximate the energy emitting member. In such implementations, the passive member, which includes a tissue contacting member and a beam blocking element that is thermally isolated from the tissue contacting member, is used to hold the tissue as the laser energy, for example, is delivered to the tissue. In such implementations, a slit in the energy emitting jaw may be used to enable radiation to pass therethrough to reach the target tissue.

Figure 12:
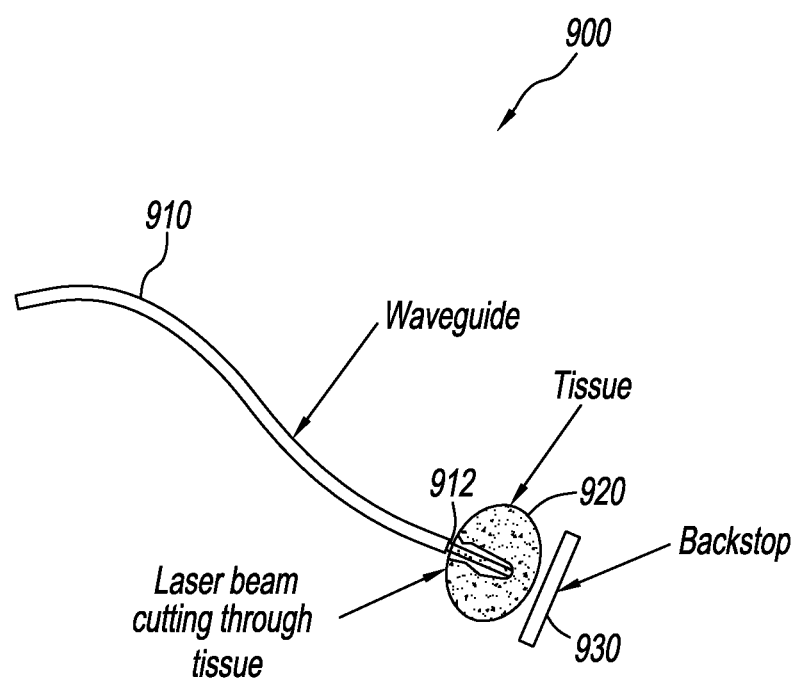
FIG. 12 is a schematic diagram of a conventional laser instrument with a backstop.

With reference to FIG. 12, showing a schematic diagram of part of a conventional laser apparatus 900, energy emitted from a tip 912 of a waveguide 910 is directed to the target tissue 920 (e.g., human tissue) and is applied thereon to perform some operation (e.g., a therapeutic operation such as cutting, coagulating, etc.) Energy that is not absorbed by the tissue reaches a backstop 930 and may heat it up. This in turn may result in the heat from the heated backstop 930 being redirected to the target tissue 920 (to the same section of the target tissue that was irradiated by the radiation emitted from the tip 912, or some other section of the target tissue) and/or parts of the apparatus 900. Consequently, such redirection of heat from the backstop 920 may reduce the quality of the operation being performed on the target tissue because heat will be directed to the instrument instead of being used for target tissue effect and, furthermore, the contacting surfaces used to hold the tissue may cause secondary damage to the target tissue in places where the target tissue should remain substantially intact. Yet another deficiency of implementations using such contacting surfaces is the tendency of such surfaces to stick to the target area (e.g., tissue) and having the target tissue stick to components of the apparatus, thus reducing their efficiency.

Figure 13A:
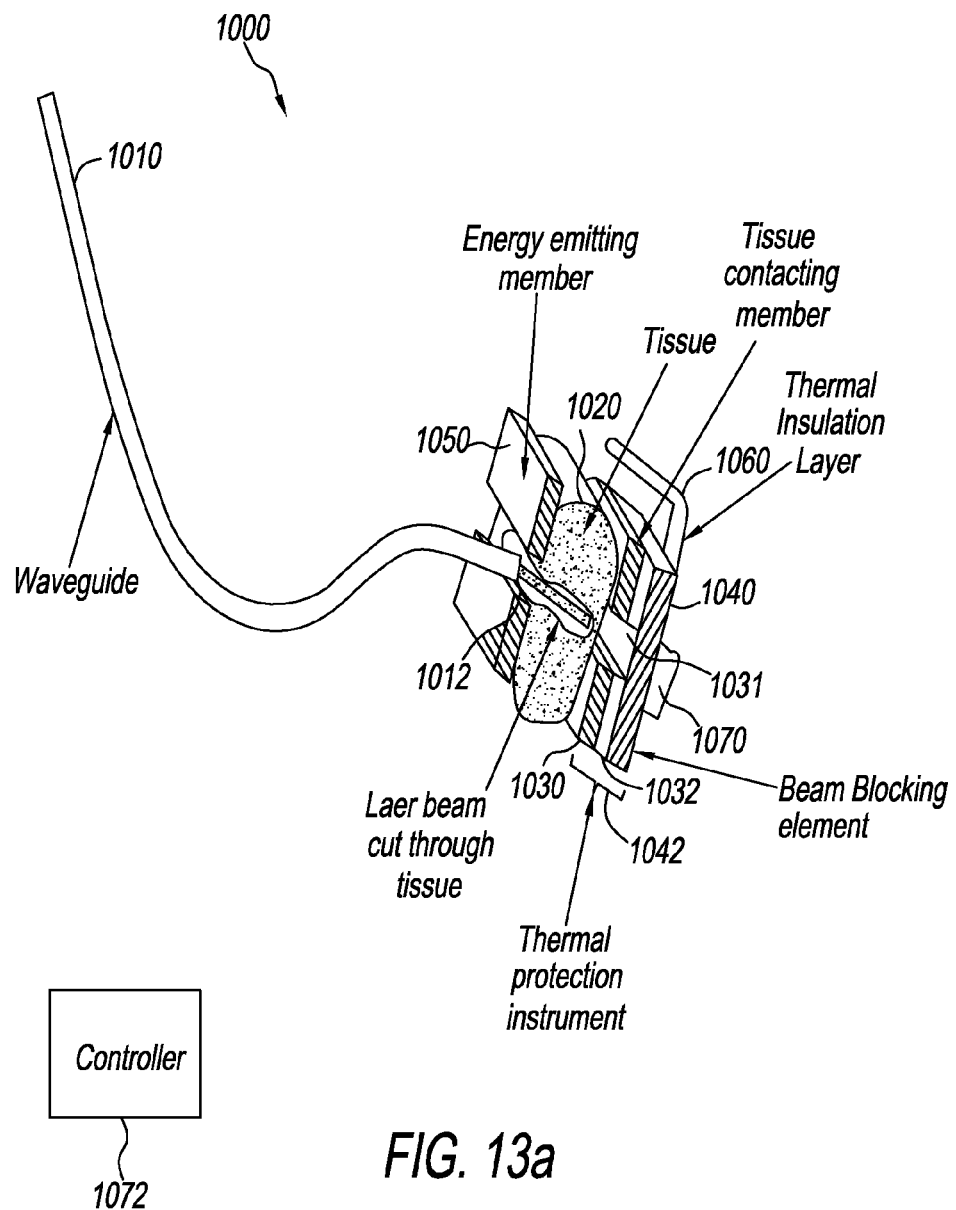
FIG. 13*a* is a schematic diagram of a laser apparatus with a thermal protection instrument (which can be either implemented in a backstop or be part of a jaw of a grasper).

With reference to FIG. 13a, a schematic diagram of a laser apparatus 1000 with a beam blocking element 1040 (also referred to as an energy blocking element/layer) that is thermally isolated from a target tissue (e.g., treated tissue) is shown. As can be seen in the figure, as well as in the cross-sectional diagram of FIG. 13b, tissue 1020 is held, or supported, by a tissue contacting member 1030 (such as a plate or a jaw), which is coupled, directly or indirectly, to the beam blocking element 1040. The tissue contacting member contacts at least part of a tissue irradiated with radiation emitted from a tip 1012 of a waveguide 1010. In some embodiments, the beam blocking element 1040 is thermally isolated from the tissue contacting member 1030 using an interfacing middle insulation layer 1032 that is coupled to the externally-located beam blocking element 1040 and to the inner surface contacting member 1030. Thus, energy absorbed by the beam blocking element 1040 (e.g., heat created during a cutting process, or some other therapeutic operation) is prevented from being redirected back to the tissue by the insulation layer 1032. In some embodiments, the member 1030 itself may be constructed from a thermal insulation material(s). Suitable materials to construct the insulation layer include such thermal insulators as ceramics, plastic, air layer, glass, wax, etc. Suitable materials to construct the beam blocking element include various metallic materials. Specific choice of materials may enable combining one or more layers of the thermal protection instrument into one, thus simplifying the implementation.

Figure 13B:
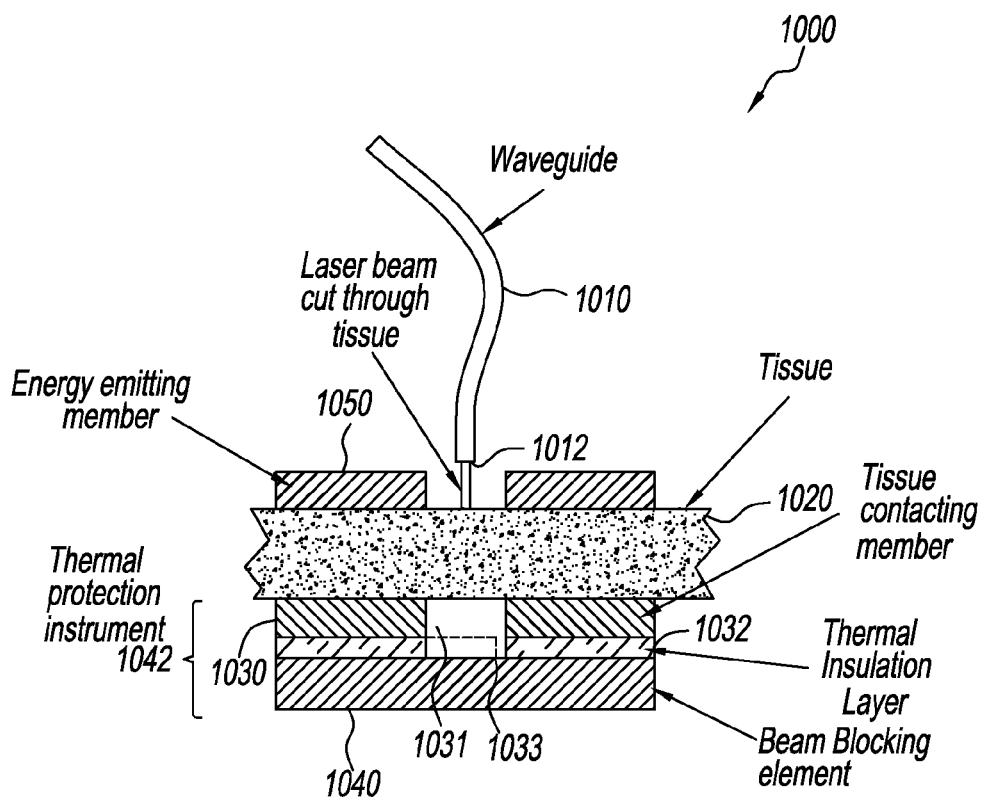
FIG. 13*b* is a cross-sectional diagram of part of the laser apparatus of FIG. 13*a*.

The tissue contacting member 1030, the thermal insulation layer 1032 and the beam blocking element 1040 may together comprise a thermal protection instrument which may be part of a grasping device, as shown in FIGS. 13a-b, or may be used as a stand-alone backstop. When used as part of a grasping device, the thermal protection instrument (comprising the tissue contacting member 1030, the optional insulation layer 1032 and the beam blocking elements 1040) is used as one of the members, or jaws, of a grasping device. When used as a stand-alone backstop, the thermal protection instrument may be coupled to a supporting structure (such as a rigid shaft), and be moved independently of other instruments to protect particular tissue areas from radiation, thermal damage, etc.

As further shown in FIGS. 13a-b, in some implementations, emitted energy (e.g., radiation) not absorbed by the target tissue 1020 passes through a slit/opening or window 1031 defined in the tissue contacting member 1030 and is directed through an overlapping (at least partly overlapping) slit or window 1033 (see FIG. 13b) defined in the insulation layer, and is applied to the beam blocking element 1040. The opening (in the tissue contacting member and/or in the thermal insulation layer) enables at least some of the radiation not absorbed by the area of the target tissue to reach the beam blocking element.

As shown, in the embodiments of FIGS. 13a-b the thermal protection instrument may be used as one of the jaws in a grasping device. The apparatus 1000 thus includes the tissue contacting member 1030 serving as a member that is opposite a grasping member 1050 that is coupled to the emitting end of the waveguide (thus, in this description the tissue contacting member 1030 may be referred to as the opposite member, while the grasping member 1050 may be referred to as an energy emitting member). The two grasping members, or jaws, hold the tissue in place to perform some therapeutic operation thereon. However, some configurations of the grasping devices may be implemented without an energy emitting grasping member. For example, in a J hook device, the energy emitting (or proximal) jaw is not included.

In some embodiments, the beam blocking element may further include another heat insulation layer (not shown) constituting an external layer of the beam blocking element structure, to prevent thermal damage to neighboring tissue due to accidental contact of the beam blocking element with the neighboring tissue.

The waveguide 1010 may be a flexible waveguide such as an optical fiber that can be either solid or hollow, may include other types of waveguides, and may be similar to any of the waveguides described in relation to FIGS. 1-10.

In some embodiments, the waveguide 1010 may be controlled using a beam controller, for example, to irradiate different locations of the target tissue being treated to effect the therapeutic operation (e.g., cutting the tissue along a desired path) and/or to avoid situations where the emitted radiation/energy drills a hole through the tissue. Implementations of a beam controller may include any of the beam controllers described herein in relation to FIGS. 1-10, including beam controllers based on the use of optical elements, such as reflectors, as described in relation to, for example, FIGS. 3 and 5-7, and/or by beam controllers to controllably displace the waveguide (linearly or radially) as described in relation to, for example, FIGS. 8-10.

The waveguide 1010 is coupled to a laser source (not shown in FIGS. 13*a-b*) which, similarly to the laser sources used in conjunction with the apparatus and devices of FIGS. 1-10, may include, a $CO_2$ laser system, a Nd:YAG laser system, a Ho:YAG laser system, Er:YAG laser system, or any other type of laser systems. Additionally, other suitable laser devices may include, in some embodiments, at least one laser diode (which may be arranged in a diode array), such as a quantum-well laser based on Antimonide (Sb) compounds such as, for example, In(Al)GaAsSb-based compounds, GaSb-based compounds, etc.

The configuration (e.g., geometry) and materials of the members (jaws) used in implementations (including the tissue contacting member and/or the energy emitting member in implementations of a grasping device) such as the ones shown in FIGS. 13*a-b* should be such that heat should not be accumulated in the beam blocking element causing its temperature to increase to a level which may result in a safety problem. Thus, in some embodiments, the heat may be transferred (e.g., via a heat removal mechanism) to a place(s) where it can be scattered to the surrounding or diffused without causing thermal damage. Various configurations of heat removal mechanisms may be implemented to remove the heat from the beam blocking element, including, for example, conducting the heat to the instrument body which may be used as a heat sink, using a thermo-electrical cooler either by directly attaching it to the beam blocking element or to some point towards which the heat can be conducted. Another option is to use heat pipes or conductors 1060 to deliver the heat to remote areas away from the apparatus.

In some embodiments, the beam blocking element may include at least one thermal sensor 1070. A signal representative of the temperature, as measured by the sensor 1070, may be provided to a user of the apparatus. In some embodiments, if the measured temperature exceeds some predetermined threshold, an indication (e.g., a beep or a visual indication) may be provided to the user. In some implementation, the thermal sensor 1070 may be used in conjunction with a controller 1072 (e.g., a processor-based controller) to implement, for example, a closed loop control mechanism to prevent overheating of the beam blocking element. In some embodiments, the beam controller and the controller 1072 may be implemented using the same processor-based device. Various implementations to prevent overheating include, but are not limited to, stopping lasing until the temperature decreases to a predefined level, reducing the laser power to a level where the beam blocking element temperature is kept nearly constant, etc. Suitable thermal sensors that may be used to control the temperature and operation of the apparatus 1000 include, for example, thermocouples, thermistors, IR sensors, etc.

In some implementations, the apparatus 1000, and/or the stand-alone thermal protection instrument, may be fitted into a supporting structure, e.g., a tubular device such as a scope-based instrument adapted to direct the apparatus to an area to be treated and to enable the apparatus.

Figure 14:
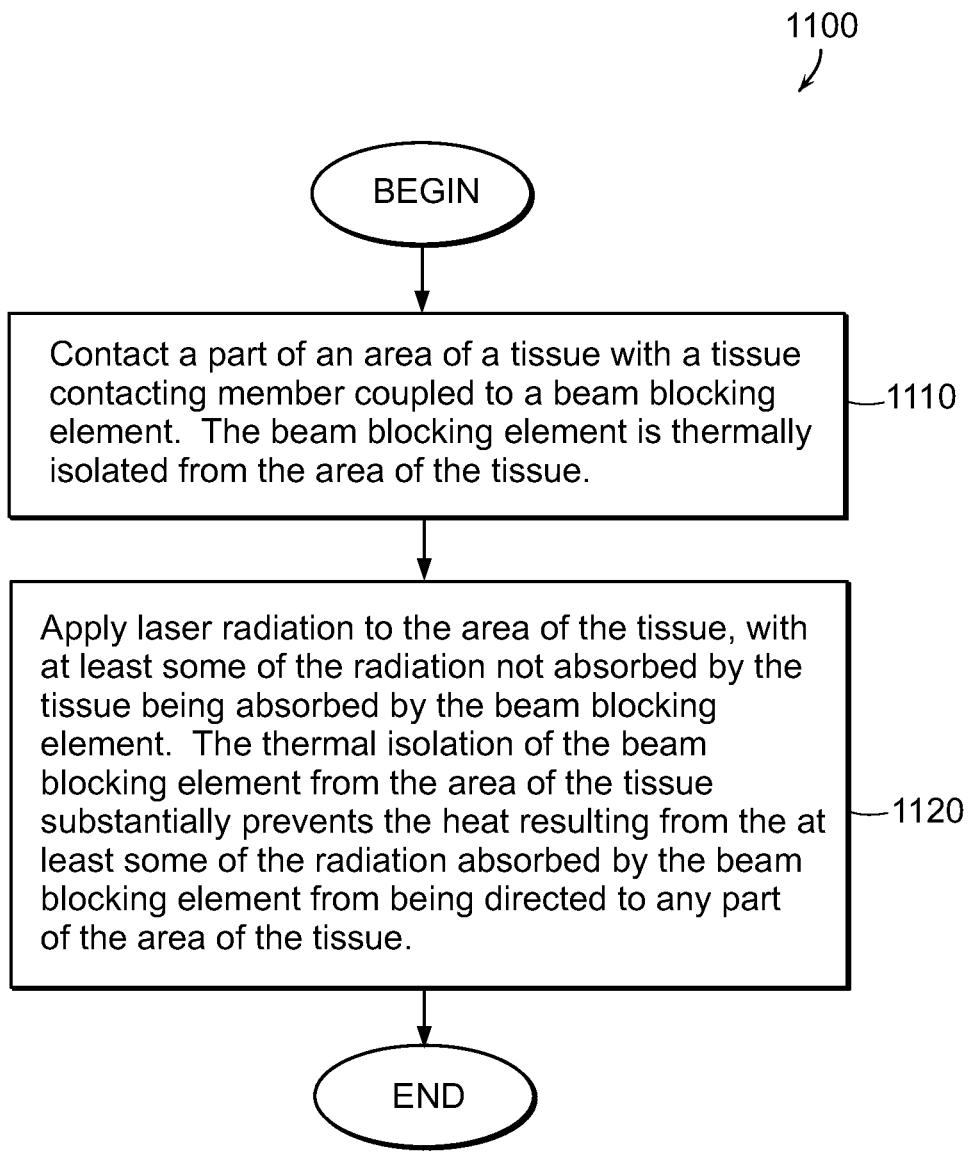
FIG. 14 is a flowchart of a procedure using a device that includes a beam blocking element that is thermally isolated from the target tissue.

With reference to FIG. 14, a flowchart of a procedure 1100 is shown. An area of a tissue (the tissue that is to be treated, e.g., perform a cutting operation, ablating operation, coagulating operation, etc.), is contacted 1110 by a tissue contacting member, such as the member 1030 shown in FIGS. 13*a-b*. The tissue contacting member is coupled to a beam blocking element that is thermally isolated (e.g., using a thermal insulation layer) from the area of the tissue to be treated. Thus, energy (e.g., in the form heat) absorbed by the beam blocking element is not delivered back to the target tissue. The tissue contacting member and the beam blocking element (and, in some embodiments, the insulation layer placed between the two) may constitute a thermal protection instrument that may be used independently of the apparatus depicted, for example, in FIGS. 13*a-b*. In some embodiments, the tissue contacting member holds (or supports) the target tissue to keep it in place while energy is applied to at least a section of the target tissue.

Subsequently, energy, such as laser radiation, is applied 1120 to at least a section of the target tissue. At least some of the radiation energy not absorbed by the target tissue may be absorbed by the beam blocking element. The thermal isolation of the beam blocking element from the tissue contacting member substantially prevents heat resulting from the at least some of the radiation absorbed by the beam blocking element from being directed to any part of the area of the tissue being treated (and, in some embodiment, prevent heat from being directed to any tissue). In some implementations, energy not absorbed by the target tissue, for example, laser radiation that passes through the target tissue, passes through a slit or a window defined in the tissue contacting member.

OTHER EMBODIMENTS

A number of embodiments have been described. Nevertheless, it will be understood that various modifications may be made without departing from the spirit and scope of the invention. Accordingly, other embodiments are within the scope of the following claims.

What is claimed is:

1. An apparatus comprising:
    a waveguide coupleable to a laser source generating laser radiation; and
    a thermal protection instrument including:
        a tissue contacting member to contact a part of an area of a tissue irradiated by laser radiation emitted from an emitting end of the waveguide, and
        a beam blocking element to absorb at least some of radiation not absorbed by the area of the tissue after having passed through the area of the tissue, the beam blocking element being thermally isolated from the area of the tissue; and,
    wherein the thermal protection instrument further comprises a thermal insulation layer positioned between the tissue contacting member and the beam blocking member; and,
    wherein the thermal insulation layer comprises an external thermal insulation coupled to an external-facing surface of the beam blocking element, the external thermal insulation layer configured to prevent thermal damage to neighboring tissue areas.

2. The apparatus of claim 1, wherein the tissue contacting member includes an opening to enable the at least some of the radiation not absorbed by the area of the tissue to reach the beam blocking element.

3. The apparatus of claim 1, wherein the tissue contacting member and the thermal insulation layer include at least partly overlapping respective openings to enable the at least some of the radiation not absorbed by the area of the tissue to reach the beam blocking element.

4. The apparatus of claim 1, wherein the thermal protection instrument is a backstop coupleable to a supporting structure.

5. The apparatus of claim 1, further comprising:
   a grasping device including:
      an energy emitting member coupled to the emitting end of the waveguide, the energy emitting member configured to grasp another part of the area of the tissue being treated; and
      wherein the tissue contacting member of the thermal protection instrument is positioned opposite the energy emitting member.

6. The apparatus of claim 5, wherein the radiation emitted from the emitting end of the waveguide is passed through an opening defined in the energy emitting member before the radiation is applied to the area of the tissue being irradiated, and wherein the at least some of the radiation not absorbed by the area of the tissue is passed through another opening defined in the tissue contacting member such that the at least some of the radiation not absorbed by the area of the tissue is received by the beam blocking element.

7. The apparatus of claim 1 further comprising:
   a beam controller to control direction of the radiation emitted by the waveguide to apply the radiation to different locations of the area of the tissue, the beam controller including one or more of:
   a reflector to direct the radiation emitted from the emitting end of the waveguide to the area of the tissue, an actuator to actuate at least the emitting end of the waveguide to cause the emitting end of the waveguide to spatially move, and
   a controllably displaceable scanning tip coupled to the waveguide, and an actuator to actuate the scanning tip, the actuation of the scanning tip causing the scanning tip to be controllably displaced to apply the radiation energy delivered via the waveguide to different locations of the area of the tissue in a scanning pattern.

8. The apparatus of claim 1, further comprising: a heat removal mechanism to remove heat resulting from at least some of the absorbed radiation from the beam blocking element.

9. The apparatus of claim 1, further comprising:
   a thermal sensor to measure the temperature of the beam blocking element.

10. The apparatus of claim 9, further comprising a controller to control the radiation emitted from the emitting end of the waveguide based on the measured temperature of the beam blocking element.

* * * * *